US010994010B2

(12) United States Patent
Zirlik et al.

(10) Patent No.: US 10,994,010 B2
(45) Date of Patent: May 4, 2021

(54) SELECTIVE TARGETING OF THE CD40L/MAC-1 INTERACTION BY SMALL PEPTIDE INHIBITORS AND ITS USE FOR THE TREATMENT OF INFLAMMATION AND ATHEROGENESIS

(71) Applicants: Universitaetsklinikum Freiburg, Freiburg (DE); Baker IDI Heart & Diabetes Institute Holdings Ltd., Melbourne (AU)

(72) Inventors: Andreas Zirlik, Freiburg (DE); Dennis Wolf, Freiburg (DE); Karlheinz Peter, Melbourne (AU)

(73) Assignees: UNIVERSITAETSKLINIKUM FREIBURG, Freiburg (DE); BAKER IDI HEART & DIABETES INSTITUTE HOLDINGS LTD., Melbourne (AU)

( * ) Notice: Subject to any disclaimer, the term of this patent is extended or adjusted under 35 U.S.C. 154(b) by 0 days.

(21) Appl. No.: 16/702,692

(22) Filed: Dec. 4, 2019

(65) Prior Publication Data

US 2020/0093924 A1 Mar. 26, 2020

Related U.S. Application Data

(60) Continuation of application No. 15/710,292, filed on Sep. 20, 2017, now abandoned, which is a division of application No. 13/880,498, filed as application No. PCT/EP2011/064132 on Aug. 17, 2011, now Pat. No. 9,808,522.

(30) Foreign Application Priority Data

Oct. 21, 2010 (EP) .................................... 10188325

(51) Int. Cl.

| | |
|---|---|
| ***C12N 5/20*** | (2006.01) |
| ***C12N 15/00*** | (2006.01) |
| ***A61K 39/00*** | (2006.01) |
| ***A61K 39/395*** | (2006.01) |
| ***A61K 38/17*** | (2006.01) |
| ***C07K 16/28*** | (2006.01) |
| ***A61K 38/08*** | (2019.01) |
| ***A61K 38/10*** | (2006.01) |
| ***A61K 38/12*** | (2006.01) |
| ***C07K 16/24*** | (2006.01) |

(52) U.S. Cl.

CPC .......... *A61K 39/3955* (2013.01); *A61K 38/08* (2013.01); *A61K 38/10* (2013.01); *A61K 38/12* (2013.01); *A61K 38/1709* (2013.01); *C07K 16/241* (2013.01); *C07K 16/2845* (2013.01); *C07K 2317/33* (2013.01); *C07K 2317/34* (2013.01); *C07K 2317/70* (2013.01); *C07K 2317/76* (2013.01)

(58) Field of Classification Search

None

See application file for complete search history.

(56) References Cited

U.S. PATENT DOCUMENTS

| | | | |
|---|---|---|---|
| 5,654,403 | A | 8/1997 | Smith et al. |
| 2004/0127416 | A1 | 7/2004 | Massia et al. |
| 2010/0144641 | A1 | 6/2010 | Popel et al. |

FOREIGN PATENT DOCUMENTS

| | | | |
|---|---|---|---|
| WO | WO 91/19511 | A1 | 12/1991 |
| WO | WO 2004/045542 | A2 | 6/2004 |
| WO | WO 2012/052205 | A1 | 4/2012 |

OTHER PUBLICATIONS

Plescia et al. Molecular Identification of the Cross-reacting Epitope on αMβ2 Integrin I Domain Recognized by Anti-αIIbβ3 Monoclonal Antibody 7E3 and Its Involvement in Leukocyte Adherence. Journal of Biological Chemistry 273(32):20372-7, 1998 • (Year: 1998).*

PCT/EP2011/064132—International Search Report, dated Dec. 6, 2011.

PCT/EP2011/064132—International Written Opinion, dated Dec. 6, 2011.

PCT/EP2011/064132—International Preliminary Report on Patentability, dated May 2, 2013.

Andre et al., "CD40L Stabilizes Arterial Thrombi by a β3 Integrin-Dependent Mechanism", Nature Medicine, vol. 8, 2002, pp. 247-252.

Li Guohong et al., "CD40 Ligand Promotes Mac-1 Expression, Leukocyte Recruitment and Neointima Formation after Vascular Injury", American Journal of Pathology, vol. 172, No. 4, Apr. 2008, pp. 1141-1152.

Wolf et al., "Interaction of CD40L with the Leukocyte Integrin Mac-1: A New Pathway for CD40L-Mediated Inflammation in Atherogenesis", Heart, Lung and Circulation, vol. 17, No. 1, Jan. 2008, p. S240.

Zhang et al., "A Discrete Site Modulates Activation of I Domains", The Journal of Biological Chemistry, vol. 271, No. 47, Nov. 22, 1996, pp. 29953-29957.

(Continued)

*Primary Examiner* — Maher M Haddad

(74) *Attorney, Agent, or Firm* — Curatelo Sidoti Co., LPA; Salvatore A. Sidoti; Floyd Trillis, III

(57) ABSTRACT

The CD40L/Mac-1 interaction is selectively targeted by small peptide inhibitors and/or antibodies and such peptides are used for the specific treatment of inflammation and atherogenesis. In particular, pharmaceutical compositions comprising a polypeptide having the amino acid sequence EQLKKSKTL and antibodies specifically binding to an epitope are disclosed.

4 Claims, 11 Drawing Sheets

Specification includes a Sequence Listing.

(56) References Cited

OTHER PUBLICATIONS

Zhang et al., "Identification and Reconstruction of the Binding Site within aMf32 for a Specific and High Affinity Ligand, NIF", The Journal of Biological Chemistry, vol. 272, No. 28, Jul. 11, 1997, pp. 17558-17564.
Zirlik et al., "CD40 Ligand Mediates Inflammation Independently of CD40 by Interaction with Mac-1", Circulation, vol. 115, No. 12, Mar. 2007, pp. 1571-1580.
Ehlers et al. Targeting Platelet-Leukocyte Interactions: Identification of the Integrin Mac-1 Binding Site for the Platelet Counter Receptor Glycoprotein Iba. J. Exp. Med. vol. 198, No. 7, Oct. 6, 2003 1077-1088.
Lee et al. Identification of a discrete region of the G protein gamma subunit conferring selectivity in beta gamma complex formation. J Biol Chem. Apr. 14, 1995;270(15):8779-84. (Year: 1995).
Simpson et al. Reduction of experimental canine myocardial reperfusion injury by a monoclonal antibody (anti-Mo1, anti-CD11b) that inhibits leukocyte adhesion. J Clin Invest. Feb. 1988;81 (2):624-9. (Year: 1988).
Bost Kl, Pascual Dw. Antibodies against a peptide sequence within the HIV envelope protein crossreacts with human interleukin-2. Immunol Invest. 17(6-7):577-86, 1988. (Year: 1988).

* cited by examiner p=0.73
p=0.03
p=0.03
Intimal wall area (mm²)
saline
cM7
scM7
p=0.52
p=0.01
p=0.056
% ORO-positive area
saline
cM7
scM7
Oil-Red-O Mac-3

α-Actin

Picrosirius p=0.10
p=0.04
p<0.001
% ORO-positive area / total wall area
p=0.83
p<0.001
p=0.001
% Mac-3-positive area / total wall area Fig. 4E
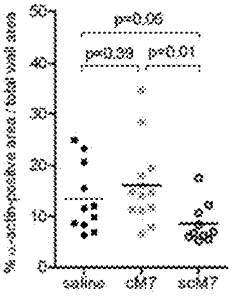
Fig. 4F
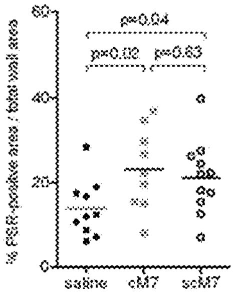
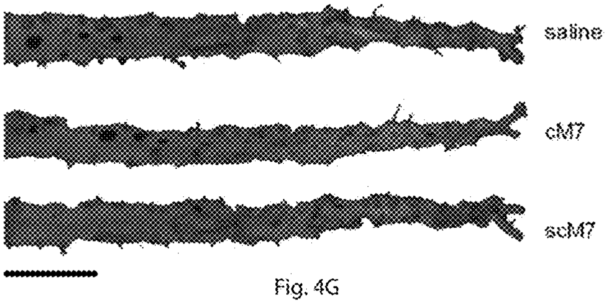
Fig. 4G
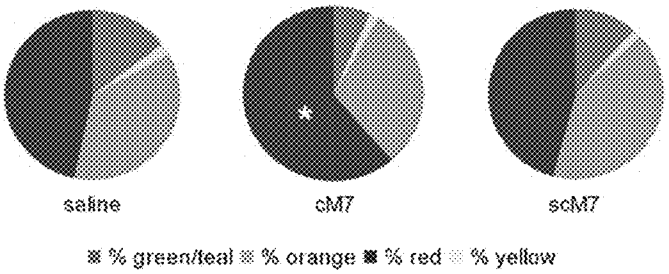
Fig. 4G
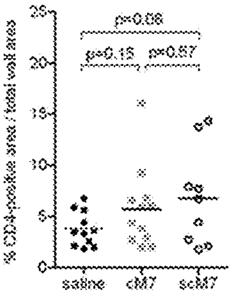
Fig. 4H
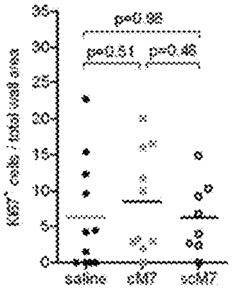
Fig. 4I Fig. 5A
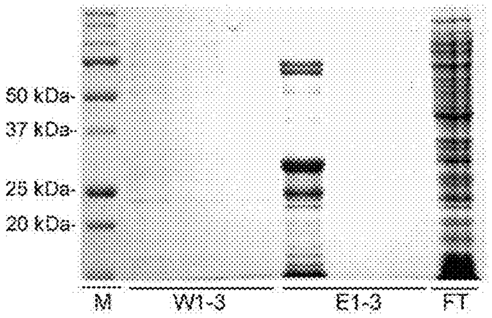
Fig. 5B
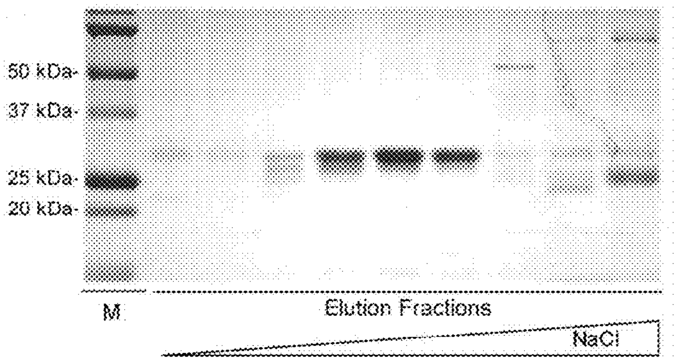
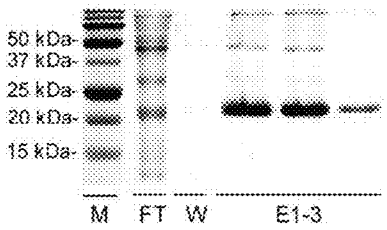
Fig. 5C Fig. 7A
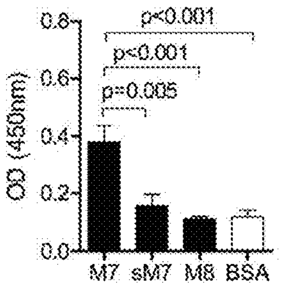
Fig. 7B
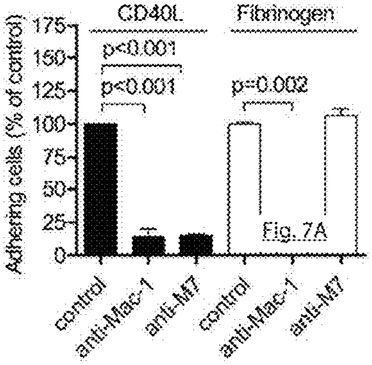
Fig. 7B
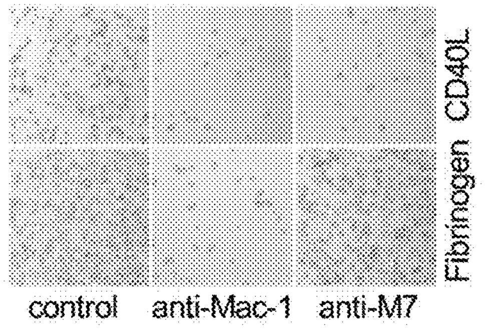
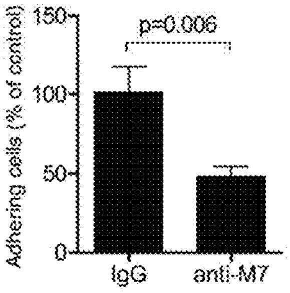
Fig. 7C Fig. 8A
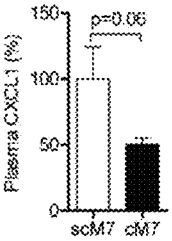
Fig. 8B
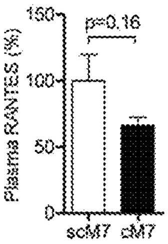
Fig. 8C
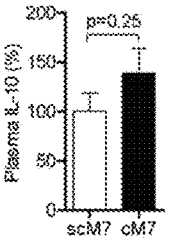
Fig. 8D
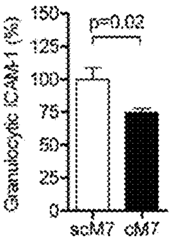
Fig. 8E
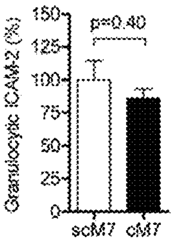
Fig. 8F
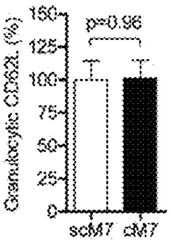
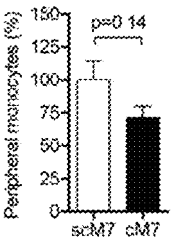
Fig. 8G
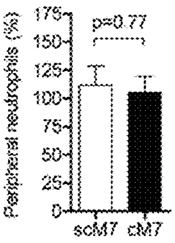
Fig. 8H
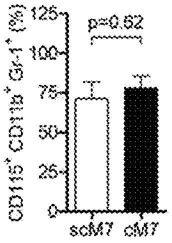
Fig. 8I

Fig. 10A

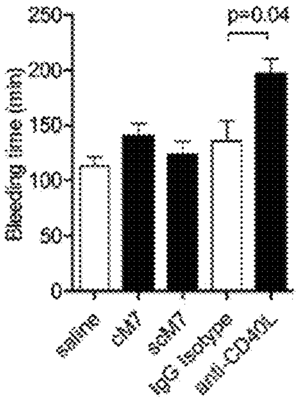

Fig. 10B

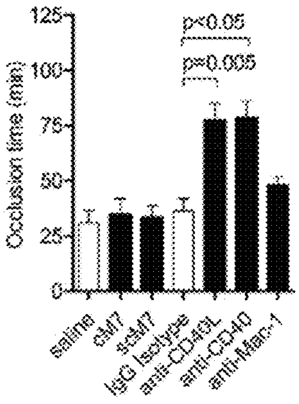

Fig. 10C

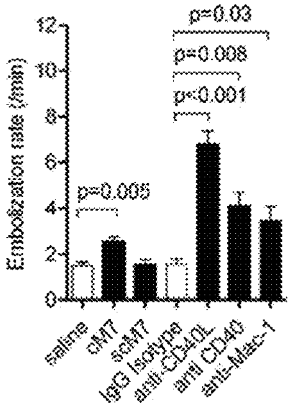

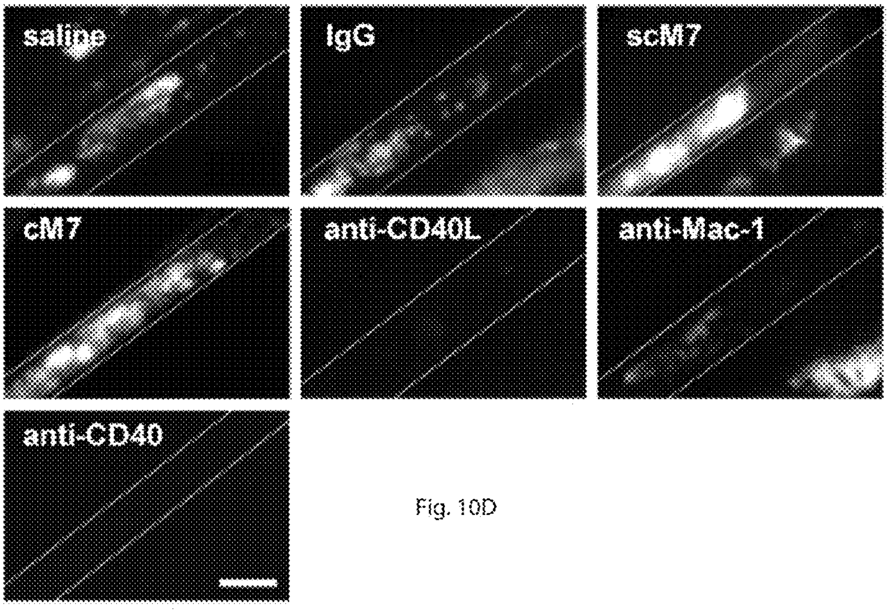

Fig. 10D

CD40/Mac-1 interaction does not mediate thrombus formation and stability in mice. C57Bl/6 wild-type mice were injected with the peptides cM7, scM7 (100μg), blocking antibodies against Mac-1, CD40L, CD40 (100μg), IgG isotype control (100μg), or saline, before assessment of tail bleeding time (A) and *in vivo* thrombus formation (B-D) in mesenteric arteriols following injury with ferrichloride. Thromboembolization rate was defined as frequency of emboli/min (C,D). Data are presented as mean±SEM of at least 4 animals per group. Scal bar 200μm.

SEQUENCE LISTING

<160> NUMBER OF SEQ ID NOS: 20

<210> SEQ ID NO 1
<211> LENGTH: 9
<212> TYPE: PRT
<213> ORGANISM: artificial sequence
<220> FEATURE:
<223> OTHER INFORMATION: therapeutically usable peptide

<400> SEQUENCE: 1

Glu Gln Leu Lys Lys Ser Lys Thr Leu
1 5

<210> SEQ ID NO 2
<211> LENGTH: 11
<212> TYPE: PRT
<213> ORGANISM: artificial sequence
<220> FEATURE:
<223> OTHER INFORMATION: therapeutically usable peptide

<400> SEQUENCE: 2

Cys Glu Gln Leu Lys Lys Ser Lys Thr Leu Cys
1 5 10

<210> SEQ ID NO 3
<211> LENGTH: 13
<212> TYPE: PRT
<213> ORGANISM: artificial sequence
<220> FEATURE:
<223> OTHER INFORMATION: epitop comprising peptide

<400> SEQUENCE: 3

Val Met Glu Gln Leu Lys Lys Ser Lys Thr Leu Phe Ser
1 5 10

<210> SEQ ID NO 4
<211> LENGTH: 19
<212> TYPE: DNA
<213> ORGANISM: artificial sequence
<220> FEATURE:
<223> OTHER INFORMATION: primer

<400> SEQUENCE: 4
agaagttccc agaggccct 19

<210> SEQ ID NO 5
<211> LENGTH: 33
<212> TYPE: DNA
<213> ORGANISM: artificial sequence
<220> FEATURE:
<223> OTHER INFORMATION: primer

<400> SEQUENCE: 5
gagtgcggcc gcggcagcgc tgaagccttc ctg 33

<210> SEQ ID NO 6
<211> LENGTH: 40
<212> TYPE: DNA
<213> ORGANISM: artificial sequence
<220> FEATURE:
<223> OTHER INFORMATION: primer

<400> SEQUENCE: 6
cctaggcggc cgctatcaga gtttgagtaa gccaaaggac 40

<210> SEQ ID NO 7

-continued

<211> LENGTH: 32
<212> TYPE: DNA
<213> ORGANISM: artificial sequence
<220> FEATURE:
<223> OTHER INFORMATION: primer

<400> SEQUENCE: 7
cttctagaaa acagctttga aatgcaaaaa ga 32

<210> SEQ ID NO 8
<211> LENGTH: 37
<212> TYPE: DNA
<213> ORGANISM: artificial sequence
<220> FEATURE:
<223> OTHER INFORMATION: primer

<400> SEQUENCE: 8
ccggccatgg ccgaacaaaa gctgatctca gaagaag 37

<210> SEQ ID NO 9
<211> LENGTH: 34
<212> TYPE: DNA
<213> ORGANISM: artificial sequence
<220> FEATURE:
<223> OTHER INFORMATION: primer

<400> SEQUENCE: 9
tgaggtacct aggtgatggt gatggtgatg tgag 34

<210> SEQ ID NO 10
<211> LENGTH: 93
<212> TYPE: DNA
<213> ORGANISM: artificial sequence
<220> FEATURE:
<223> OTHER INFORMATION: primer

<400> SEQUENCE: 10
atgaaacaga ttgaagataa aattgaagaa attctgagca aaatttatca tattgaaaac 60
gaaattgcgc gtattaaaaa actgattgga gaa 93

<210> SEQ ID NO 11
<211> LENGTH: 13
<212> TYPE: PRT
<213> ORGANISM: artificial sequence
<220> FEATURE:
<223> OTHER INFORMATION: therapeutically usable peptide

<400> SEQUENCE: 11

Pro His Asp Phe Arg Arg Met Lys Glu Phe Val Ser Thr
1 5 10

<210> SEQ ID NO 12
<211> LENGTH: 17
<212> TYPE: PRT
<213> ORGANISM: artificial sequence
<220> FEATURE:
<223> OTHER INFORMATION: therapeutically active peptide

<400> SEQUENCE: 12

Pro Ile Thr Gln Leu Leu Gly Arg Thr His Thr Ala Thr Gly Ile Arg
1 5 10 15

Lys

<210> SEQ ID NO 13
<211> LENGTH: 17

-continued

```
<212> TYPE: PRT
<213> ORGANISM: artificial sequence
<220> FEATURE:
<223> OTHER INFORMATION: therapeutically active peptide

<400> SEQUENCE: 13

Lys Phe Gly Asp Pro Leu Gly Tyr Glu Asp Val Ile Pro Glu Ala Asp
1               5                   10                  15

Arg


<210> SEQ ID NO 14
<211> LENGTH: 15
<212> TYPE: PRT
<213> ORGANISM: artificial sequence
<220> FEATURE:
<223> OTHER INFORMATION: therapeutically active peptide

<400> SEQUENCE: 14

Asp Ala Phe Arg Ser Glu Lys Ser Arg Gln Glu Leu Asn Thr Ile
1               5                   10                  15


<210> SEQ ID NO 15
<211> LENGTH: 11
<212> TYPE: PRT
<213> ORGANISM: artificial sequence
<220> FEATURE:
<223> OTHER INFORMATION: therapeutically active peptide

<400> SEQUENCE: 15

Phe Gln Val Asn Asn Phe Glu Ala Leu Lys Thr
1               5                   10


<210> SEQ ID NO 16
<211> LENGTH: 8
<212> TYPE: PRT
<213> ORGANISM: artificial sequence
<220> FEATURE:
<223> OTHER INFORMATION: therapeutically active peptide

<400> SEQUENCE: 16

Gln Asn Asn Pro Asn Pro Arg Ser
1               5


<210> SEQ ID NO 17
<211> LENGTH: 8
<212> TYPE: PRT
<213> ORGANISM: artificial sequence
<220> FEATURE:
<223> OTHER INFORMATION: therapeutically active peptide

<400> SEQUENCE: 17

Glu Glu Phe Arg Ile His Phe Thr
1               5


<210> SEQ ID NO 18
<211> LENGTH: 9
<212> TYPE: PRT
<213> ORGANISM: artificial sequence
<220> FEATURE:
<223> OTHER INFORMATION: therapeutically active peptide

<400> SEQUENCE: 18

Lys Leu Ser Leu Glu Lys Gln Thr Lys
1               5


<210> SEQ ID NO 19
```

```
<211> LENGTH: 5
<212> TYPE: PRT
<213> ORGANISM: artificial sequence
<220> FEATURE:
<223> OTHER INFORMATION: therapeutically active peptide

<400> SEQUENCE: 19

Glu Gln Leu Lys Lys
1               5


<210> SEQ ID NO 20
<211> LENGTH: 7
<212> TYPE: PRT
<213> ORGANISM: artificial sequence
<220> FEATURE:
<223> OTHER INFORMATION: therapeutically active peptide

<400> SEQUENCE: 20

Cys Glu Gln Leu Lys Lys Cys
1               5
```

SELECTIVE TARGETING OF THE CD40L/MAC-1 INTERACTION BY SMALL PEPTIDE INHIBITORS AND ITS USE FOR THE TREATMENT OF INFLAMMATION AND ATHEROGENESIS

This application is a continuation of U.S. Ser. No. 15/710,292, filed Sep. 20, 2017, which is a divisional of U.S. Ser. No. 13/880,498, filed Jun. 28, 2013, now U.S. Pat. No. 9,808,522, which is a US National Stage application under 35 U.S.C. § 371 of International Application No. PCT/EP2011/064132, filed Aug. 17, 2011, which claims priority from European Patent Application No. 10188325.4, filed Oct. 21, 2010, from which applications priority is claimed, and which are incorporated herein by reference.

The present invention relates to CD40 ligand (CD40L) which plays a role in diseases associated with inflammation and atherogenesis. CD40 ligand, also known as human CD154, is a 33 kDa type II transmembrane protein and is a member of the tumor necrosis factor (TNF) gene superfamily. Although CD40L is expressed preferentially on activated $CD4^+$ T-cells and activated platelets, it is also found on other hematopoietic and non-hematopoietic cells such as epithelial and endothelial cells.

In a similar manner to all other members of the TNF family membrane-bound CD40L exists in a trimeric form, which is essential for the full biological activity of the molecule. Soluble CD40L mainly appears as monomer in blood but will trimerize in higher concentrations. CD40L was initially identified as ligand for CD40, but more recently additional receptors for CD40 have been described, namely the integrins αIIbβ3, α5β1 and Mac-1.

Macrophage-1 antigen (Mac-1) is also known as integrin aM (ITGAM) which is one protein subunit that forms the heterodimeric integrin αMβ-2 ($\alpha_M\beta_2$) molecule. $\alpha_M\beta_2$ is expressed on the surface of many leukocytes involved in the innate immune system, including monocytes, granulocytes, macrophages and natural killer cells. It mediates inflammation by regulating leukocyte adhesion and migration and has been implicated in several immune processes such as phagocytosis, cell-mediated cytotoxicity, chemotaxis and cellular activation.

CD40L participates in chronic inflammatory diseases such as atherosclerosis. Through interaction with its classic receptor CD40, CD40L regulates B-cell and T-cell function. CD40L also stabilizes thrombi through interaction with the platelet integrin $\alpha_{IIb}\beta_3$. While anti-CD40L antibody treatment generated promising results in early clinical trials, elevated thromboembolic complications prohibited the pursuit of this strategy. In addition, long-term inhibition of CD40L—as is most likely required for treatment of chronic inflammatory diseases—severely compromises host defenses, rendering generalized inhibition of CD40L an unappealing treatment strategy. Zirlik et al., Circulation, 2007, 1571-1580 previously reported that CD40L mediates atherogenesis independently of CD40 in mice, and proposed a novel interaction with the leukocyte integrin Mac-1. In this article it is not disclosed where the interaction of the whole Mac-1 protein and CD40L takes place in vitro. No targeting by peptides or specific antibodies was attempted.

WO 2004/045542 discloses therapeutic bioconjugates comprising a hydrophilic polymer and peptides capable of binding specifically to a ligand expressed on a cell surface. The polypeptide can be derived from a huge variety of sequences, inter alia the CD11bI domain.

WO 91/19511 discloses a method of controlling phagocyte-mediated tissue damage (such as inflammation) to a human patient whereby said method comprises the administration of a therapeutic composition of a peptide comprising part of the β2 integrin subunit of CD11b. The peptides disclosed differ, however, from the peptides of the present invention. Moreover, artherosclerosis is not a primary target of this publication.

Wolf et al., "Interaction of CD40L with the Leukocyte Integrin Mac-1: A New Pathway for CD40L-Mediated Inflammation in Atherogenesis", Heart, Lung and Circulation, vol. 17, Jan. 1, 2008, p. S 240 mention the interaction of CD40L and Mac-1 as an alternative pathway for CD40L-mediated inflammation. This mechanism expands the understanding of inflammatory signaling during atherogenesis. In the abstract there is, however, no mention of the binding site and specific peptides or antibodies.

Li et al., The American Journal of Pathology, vol. 172 (2008), pp 1141-1151, describe an animal model of restenosis rather than artherosclerosis. The induction of Mac-1 expression by CD40L is disclosed, but binding between CD40L and Mac-1 or any therapeutic use thereof is not disclosed. Zhang et al., J. Biol. Chemistry (1996), pp 29953-29957, describe the identification of a discrete site within the I domain of integrin $\alpha_M\beta_2$ which modulates the adhesive activity of this receptor. This region is described as composed of two short and spatially proximal loops.

Here this interaction and its therapeutic use is characterized on a molecular level, identifying the amino acids $E^{162}$-$L^{170}$, located on an exposed loop between the al helix and β-sheet B of the Mac-1 I-domain, as a distinct binding site for CD40L. Targeting of CD40L/Mac-1 binding with a preferred stable inhibitory peptide, in the following: cM7, proved specific and ultimately effective in attenuating inflammation and atherosclerotic lesion formation in mice. Specific inhibition of the CD40L/Mac-1 interaction might therefore represent an attractive novel anti-inflammatory treatment strategy for atherosclerosis and other chronic inflammatory diseases, avoiding the unwanted effects of global inhibition of CD40 ligand action.

Chronic inflammation drives atherosclerosis. CD40L, a member of the tumor necrosis factor superfamily first described on T-cells, participates as a key regulator of atherogenesis. Functional blockade of CD40L not only reduced atherosclerotic plaque formation and progression, but also attenuated monocyte and lipid content of these lesions while increasing numbers of collagen fibers and smooth-muscle cells—features commonly associated with more stable plaques in humans. CD40L also augments monocyte/macrophage expression of collagenases implicated in plaque disruption and of tissue factor, a trigger of thrombosis following plaque rupture. The surprising finding was previously reported that CD40L promotes atherogenesis without participation of CD40L on bone marrow-derived cells, and independently of its classic receptor CD40. These findings point towards a role of CD40L on vascular cells, such as endothelial or smooth-muscle cells, interacting with an alternate receptor.

The present invention relates to the interaction of CD40L with the leukocyte integrin Mac-1, an adhesive receptor interacting with a variety of known ligands implicated in immunity, inflammation, and hemostasis. Inhibition of Mac-1 by neutralizing antibodies markedly attenuated atherosclerotic lesion formation by impairing monocyte recruitment. Here the interaction between CD40L and Mac-1 is used for potential therapeutic applications.

While inflammation drives many chronic diseases, including atherosclerosis, few selective anti-inflammatory treatment options currently exist. In the context of atherosclerosis, statins (lipid-lowering drugs that exert various anti-inflammatory actions) allow a glimpse at the therapeutic potential of such strategies. Another class of drugs, the Cox-2 inhibitors, exemplifies the impressive extent of therapeutic benefits but they also demonstrate the difficulty in developing anti-inflammatory drugs without side effects. Previous concepts aimed at the global inhibition of cytokines such as CD40L largely failed due to acute or long-term side effects.

The present invention relates to the specific inhibition of the CD40L/Mac-1 interaction by using small peptide inhibitors and/or antibodies which specifically bind to an epitope having a well-defined amino acid sequence and the use thereof in pharmaceutical compositions. The peptide comprising the sequence EQLKKSKTL (SEQ ID NO:1) mimmicks part of Mac-1's I-domain and therefore binds to its counterpart region on CD40L. The antibodies are directed against the peptide sequence (after modification) and therefore bind to EQLKKSKTL on Mac-1.

The relevant amino acid sequence has been identified in the course of the present invention and the polypeptides comprise the amino acid sequence EQLKKSKTL (SEQ ID NO:1). It is essential that the peptide to be used has the amino acid sequence as shown in SEQ ID NO:1. It is, however, possible to slightly modify the amino acid sequence, for example by replacing single amino acids. When such amino acids are replaced, the polarity of the amino acid is maintained. This means that amino acids having hydrophobic or hydrophilic character are replaced by other amino acids having the same character. It is for example possible to replace a leucin residue by an isoleucin residue or a leucin residue by an arginin. Preferably only one amino acid of SEQ ID NO:1 is replaced.

In an alternative modification one or possibly also two amino acids can be deleted whereby the biological activity is maintained. It has, however, to be carefully checked which amino acid can be deleted whereby the activity of the peptide has to be carefully monitored.

The polypeptide has not more than 15 amino acids and more preferable not more than 12 amino acids. The polypeptide of the present invention may contain on the N-terminus and/or the C-terminus thereof additional amino acids which do not negatively influence the biological activity of the polypeptide.

The experiments show that the probably most important part of the peptide sequence is the amino acid motif QLK which may be the most important part of the peptide. Therefore, antibodies which can be used for pharmaceutical purposes are preferably directed against the motif QLK. In another preferred embodiment the motif against which the antibodies are directed is EQLKK (SEQ ID NO: 19). This motif can also be used in a cyclic structure, namely CEQLKKC (SEQ ID NO: 20).

The polypeptide as used in the pharmaceutical composition must be stabilized against degradation in the patient. Either the peptide structure is chemically modified in such a manner that the normal degradation of the peptide is inhibited or at least delayed. Another preferred method of stabilizing the peptide is to form a cyclic sequence which still has the desired biological effects. The advantage of this cyclic peptide structure is the delayed degradation and therefore enhanced bioavailability. In a preferred embodiment the peptide has the amino acid sequence CEQLKKSKTLC (SEQ ID NO:2).

In a further alternative approach the N-terminus or the C-terminus is modified. One interesting approach is to bind polyethyleneglycol units (PEG) directly or preferably via a linker to the peptide molecule. This has the advantage that the stability of the molecule is increased. On the other hand the bioavailability of the modified molecule is improved since the molecule is maintained for a longer period of time in the body to be treated with the peptide. It should be mentioned, however, that by the modification the steric conformation of the molecule should not be changed in such a manner that the binding of the peptide to the target area is not inhibited.

In a further alternative embodiment the peptide sequence is at least partially replaced by peptide analoga.

The pharmaceutical compositions of the present invention can be administered in a suitable form well-known to the person skilled in the art. The composition can be administered either orally or in the form of a suitable injection. Also topical administration in form of creams or ointments is possible. In addition to the polypeptide of the present invention the pharmaceutical composition comprises commonly used additives to a pharmaceutical composition such as stabilizers, pH regulators, preservative agents and the like.

The pharmaceutical composition is preferably used in the treatment of an inflammatory disease and/or in the treatment of an atherosclerotic disease. In particular, the compositions can be preferably used for the treatment of chronic inflammatory diseases such as coronary heart disease, rheumatoid arthritis, lupus, asthma and potentially all other conditions with which CD40L has been implicated previously.

In another embodiment the present invention relates to an antibody which specifically binds to an epitope which comprises at least part of the amino acid sequence VMEQLKKSKTLFS (SEQ ID NO:3). The preferred antibody is a human antibody. Such antibodies can be prepared either by humanization of mouse antibodies or the antibodies can be obtained by the so-called phage display method. Since the epitope against which the antibody is directed is known such antibodies can be easily obtained. Such antibodies specifically bind to an epitope contained within the given sequence and therefore the antibody inhibits the adhesion of Mac-1 to CD40L. The antibodies are preferred IgG antibodies. In an alternative embodiment also binding fragments (Fab) can also be used. Such functionally active parts of antibodies are understood to be covered by the term "antibody".

The disclosed peptide-based strategy might overcome some of these limitations. CD40L has at least four different receptors, including CD40 and the integrins $\alpha_{IIb}\beta_3$, Mac-1 ($\alpha_M\beta_2$), and $\alpha_V\beta_1$. This invention uses a novel selective inhibitor to characterize receptor-dependent properties of CD40L. The use of similar strategies to block selectively other interaction partners and their defined roles in inflammation, immunology, and hemostasis, might enable development of tailored drugs for different CD40L-dependent conditions. The preferred cyclic polypeptide having SEQ ID NO:2 (cM7) was efficacious and specific in the inhibition of CD40L/Mac-1 binding and its downstream effects, such as inflammatory gene expression, inflammatory cell recruitment, and atherogenesis. Therefore, cM7 may represent a fruitful novel strategy to combat chronic inflammatory diseases such as atherosclerosis.

One of the surprising results was that the polypeptides of the present invention were able to specifically inhibit the CD40L/Mac-1 interaction without, however, provoking other unspecific and unwanted side effects. In particular the polypeptides of the present invention did not interfere with CD40L/GPIIb/IIIa mediated thrombus formation in vivo. The results disclosed in the present application support the concept of a therapeutic blockade of CD40L. Previously known concept aimed at the global inhibition of CD40L and failed due to acute or long-term side effects. In particular, clinical data revealed thromboembolic complications most likely to destabilization of thrombi [Andre et al. (2002), Nat. Med. 8, pp 247-252]. In contrast thereto the specific inhibition of the CD40L/Mac-1 interaction obtainable by the polypeptides and antibodies of the present invention hardly affected thrombose integrity. In particular cM7 did not interfere with CD40-CD40L binding in vitro and did not induce changes in basic immunological characteristics such as alteration of Th1/Th2-phenotype.

The results of the experiments are summarized in the figures and explained in more detail in the figure legends.

BRIEF DESCRIPTION OF THE DRAWINGS

FIG. 1A to FIG. 1J show that CD40L binds to a distinct site within Mac-1's I-domain.

FIG. 1A I-domain shown based on its crystal structure (INA5): left, as a ribbon diagram; right, as a model of the hydrated surface with linear peptides corresponding to sections, M1 to M8.

FIG. 1B Recombinant CD40L specifically bound to the immobilized I-domain in a solid phase binding assay.

FIG. 1C I-domain concentration-dependently bound to immobilized CD40L. The insert shows recombinant, purified CD40L and I-domain on a Coomassie Blue-stained acrylamide gel. Different clones specifically blocking Mac-1 (2LPM19c, ICRF44), CD40L (40804, 24-31), and LFA-1 (HI111) were tested for their capability to block adhesion of Mac-1 expressing CHO cells to immobilized fibrinogen FIG. 1D or

CD40L FIG. 1E.

Small peptide inhibitors, M1 to M8 (50 μM), were used to block binding of CD40L to the immobilized I-domain in a solid phase binding assay FIG. 1F (The sequences of M1 to M8 are shown in Table 1.), to block adhesion of activated THP-1 cells to immobilized CD40L in an adhesion assay FIG. 1G, and to block binding of fluorescence-labeled CD40L to freshly isolated human granulocytes and monocytes in flow cytometry FIG. 1H.

FIG. 1I Peptides M1 to M8 were immobilized to highly absorbent plastic plates, and direct binding of biotinylated CD40L was quantified.

Figure 1J:
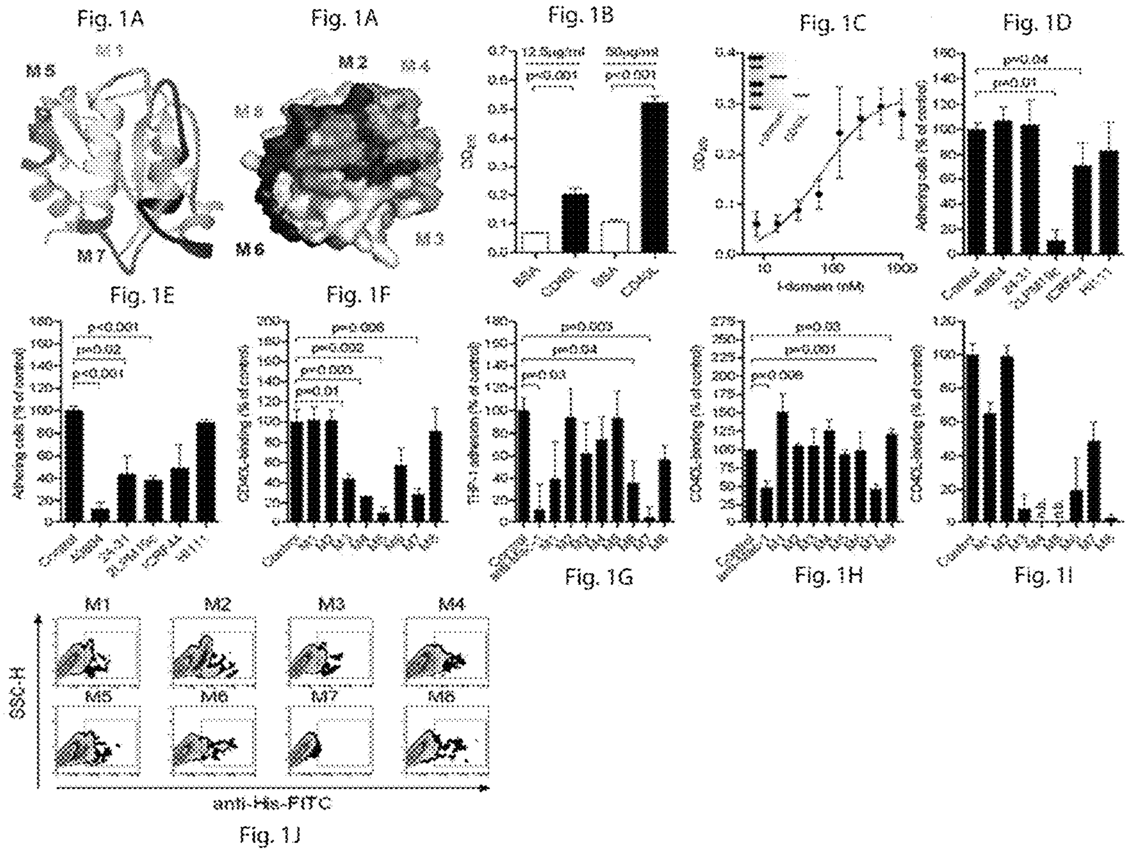

FIG. 1J I-domain peptides (50 μM) were also tested for the ability to block binding of CD40L to Mac-1 expressing CHO cells in flow cytometry, as demonstrated by representative dot plots. Data are presented as mean±SEM of at least three independent experiments (FIG. 1B, FIG. 1C, FIG. 1D, FIG. 1E, FIG. 1F, FIG. 1G, FIG. 1I). Three healthy male donors are included in FIG. 1H. n.b.: no binding FIG. 2A to FIG. 2L show the In vitro and in vivo characterization of the peptide antagonist.

Figures 2A, 2B, 2C, 2D, 2E, 2F, 2G, 2H, 2I, 2J, 2K, 2L:
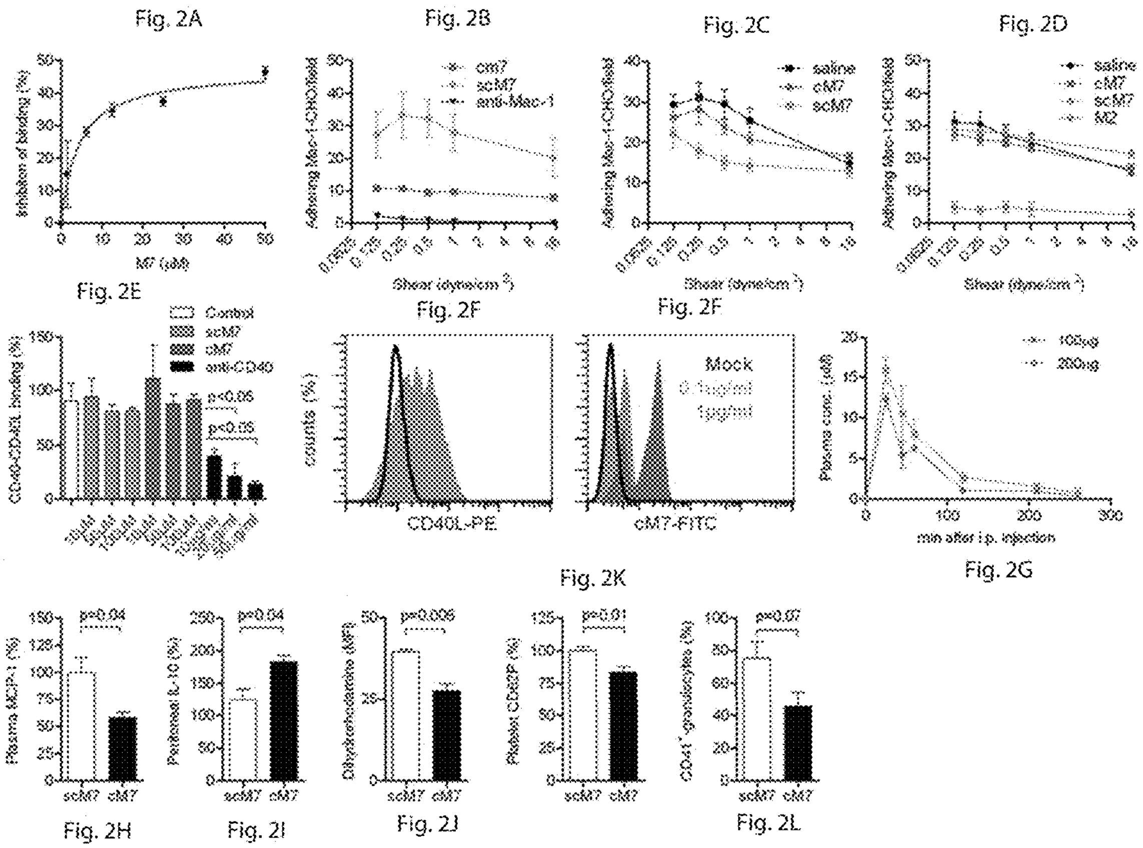

FIG. 2A The peptide M7 mimicking the CD40L/Mac-1 binding site was tested in a solid phase binding assay, and concentration-dependently inhibited CD40L binding to the immobilized I-domain.

FIG. 2B cM7, a cyclic variant of the specific peptide inhibitor M7, optimized for in vivo use, inhibited adhesion of a Mac-1 expressing CHO cell line to immobilized CD40L in a dynamic flow chamber assay. Demonstrating specificity, cM7 failed to block adhesion of Mac-1 expressing cells to the alternative Mac-1 ligands ICAM-1 FIG. 2C, and GPIbα FIG. 2D, whereas the GPIbα-specific control peptide M2 efficiently blocked adhesion to the platelet protein.

FIG. 2E cM7 and scM7 did not affect binding of CD40L to immobilized CD40-Fc fragments, whereas a blocking anti-CD40 antibody concentration dependently blocked molecular interaction.

FIG. 2F FITC-labeled cM7 specifically bound to CD40L-transfected murine fibroblasts, but not to mock-transfected fibroblasts, as demonstrated in flow cytometry.

FIG. 2G Pharmacokinetics of intraperitoneal-injected cM7.

FIG. 2H Intraperitoneal-injected cM7 attenuated the TNFα-induced inflammatory response compared with scM7 (n=8 per group) by lowering plasma levels of the chemoattractant MCP-1 and FIG. 2I increasing protective IL-10 plasma levels.

FIG. 2J Oxidative stress was reduced in granulocytes of cM7-treated animals.

FIG. 2K, FIG. 2L Platelet activation was diminished after cM7 injection, as demonstrated by decreased platelet P-selectin expression and lowered platelet-leukocyte aggregates. Data are presented as mean±SEM of at least three independent experiments.

FIG. 3A to FIG. 3L illustrate that the CD40L/Mac-1 interaction contributes to inflammatory cell recruitment in vitro and in vivo.

Figures 3A, 3B, 3C, 3D, 3E, 3F, 3G, 3H, 3I, 3J, 3K, 3L:
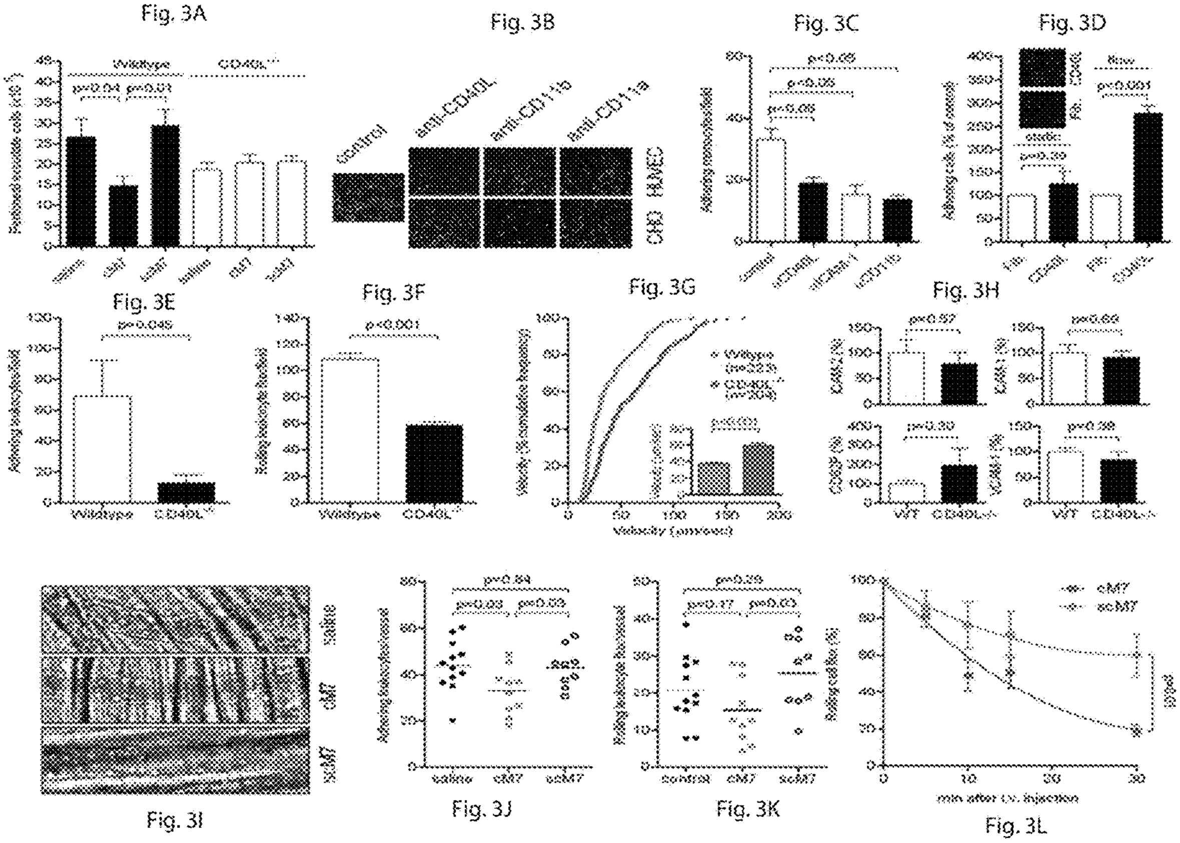

FIG. 3A Treatment of WT (wild type) mice (n=6 per group) with the specific peptide inhibitor cM7 inhibited the recruitment of thioglycollate-elicited leukocytes to the peritoneal cavity, compared with an unspecific peptide control, scM7, or a saline injection. Treatment with peptides had no effect in $CD40L^{-/-}$ mice (n=6 per group).

FIG. 3B Mac-1-expressing CHO cells were allowed to adhere on TNF-α-primed human umbilical vein endothelial cells (HUVECs), while both cell types were selectively blocked with antibodies against Mac-1, CD40L, or LFA-1.

FIG. 3C Anti-CD40L antibody blocked dynamic adhesion of human monocytes to HUVECs comparable to anti-ICAM-1 or anti-Mac-1 (n≥4).

FIG. 3D Mac-1-CHO-cells adhered to immobilized CD40L preferably under flow conditions compared with fibrinogen.

FIG. 3E, FIG. 3F, FIG. 3G Numbers of adhering and rolling murine leukocytes decreased when interacting with CD40L-deficient endothelial cells (ECs), compared with wild-type ECs (n=5 per group). The mean leukocyte rolling velocity increased on CD40L-deficient ECs.

FIG. 3H CD40L deficiency did not regulate surface expression of the adhesion molecules ICAM-1, ICAM-2, VCAM-1, or P-selectin. FIG. 3I In intravital microscopy, adhesion FIG. 3J and rolling FIG. 3K of leukocytes in TNFα-challenged mice were blocked by an intraperitoneal injection of cM7 (n=10), but not of scM7 (n=9) or saline (n=12).

FIG. 3L Injected intravenously, cM7 directly blocked leukocyte rolling in intravital microscopy. Data are presented as mean±SEM. Scale bar 20 μm FIG. 3I.

FIG. 4A to FIG. 4I show that specific blockade of the CD40L/Mac-1 interaction attenuates atherosclerosis in mice. LDLr−/− mice consumed a high-cholesterol diet for 20 weeks. Mice were injected with the specific inhibitor of the CD40L/Mac-1 interaction, cM7 (n=13), an unspecific peptide control, scM7 (n=12), or saline (n=12), three times a week.

Figures 4A, 4B, 4C, 4D, 4E, 4F:
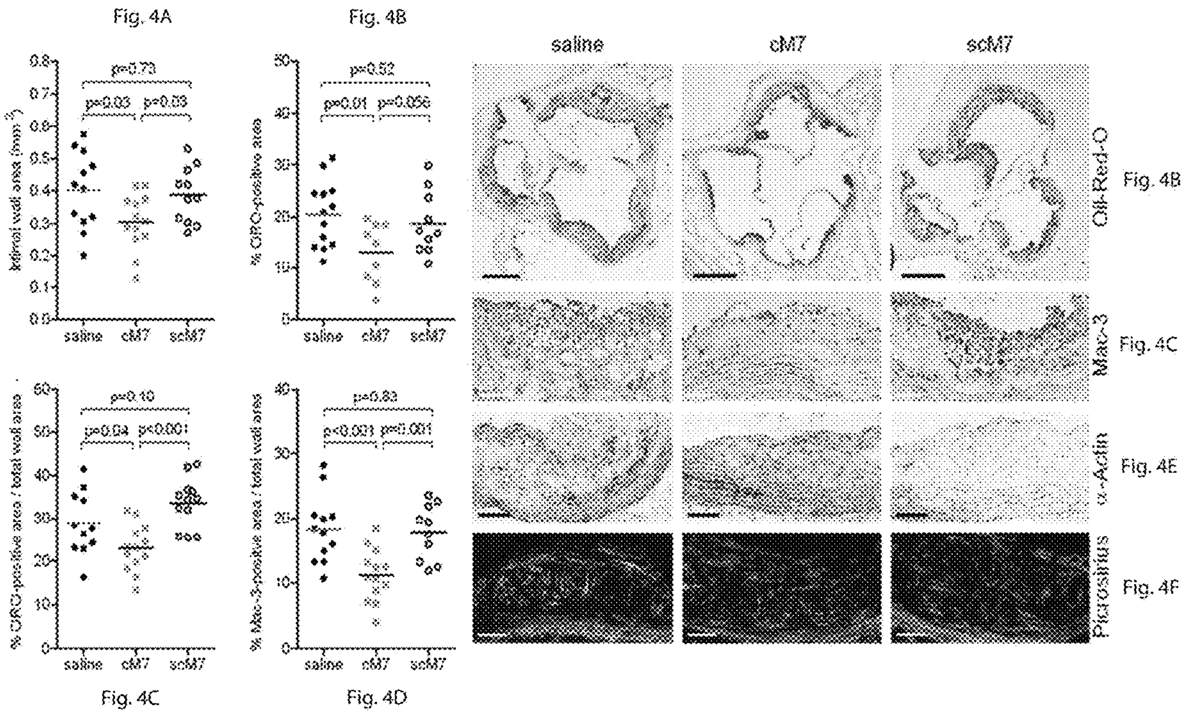
Figure 6A:
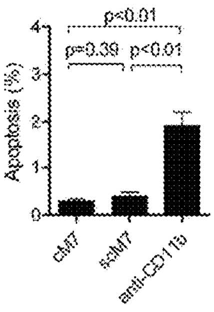
Figure 6B:
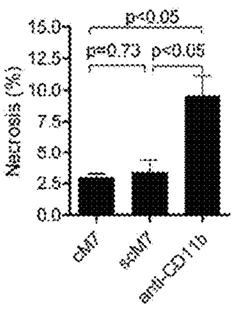
Figure 6C:
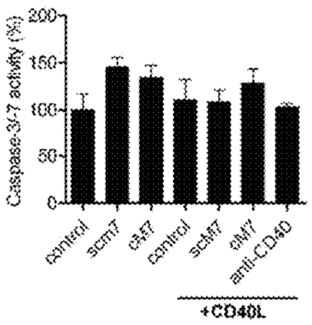
Figure 6D:
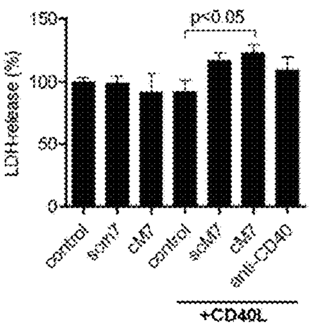
Figures 9A, 9B, 9C, 9D, 9E, 9F, 9G, 9H, 9I, 9J:
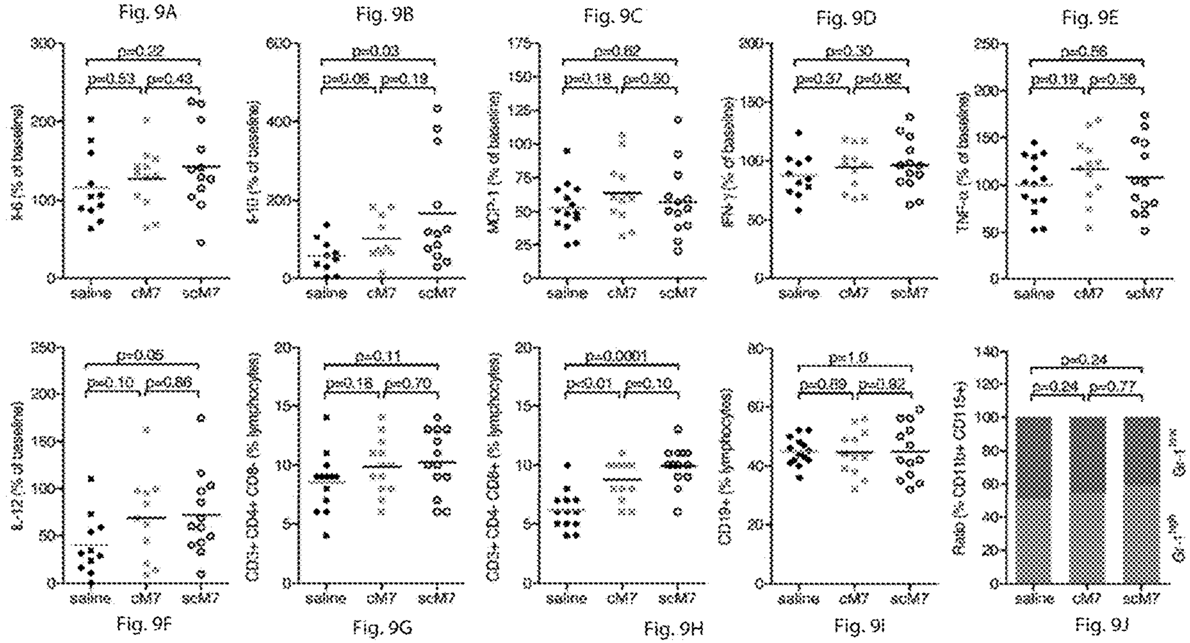

FIG. 4A cM7 significantly reduced the intimal lesion area in aortic roots compared with scM7 or the peptide control.

FIG. 4B Lipid deposition in the abdominal aorta was reduced by cM7 treatment.

FIG. 4C Lipid content in aortic roots, as assessed by quantification of Oil-red-O-positive area, was reduced in cM7-treated animals, compared with controls.

The numbers of macrophages FIG. 4D and smooth-muscle cells FIG. 4E within the atherosclerotic plaque, as well as the content of collagen FIG. 4F, were quantified by immunohistochemistry.

FIG. 4G Relative distribution of stable and unstable collagen fibers was determined by polarizing microscopy using picrosirius-red staining. cM7-treated animals exhibited a significantly higher percentage of red-polarizing, stable collagen fibers, compared with scM7-treated and saline-treated mice ($p=0.0081$ vs. saline, $p=0.0140$ vs. scM7; $n \geq 9$ per group).

FIG. 4H T-cell content and the proliferation marker Ki-67 FIG. 4I were quantified in atherosclerotic sections. Data are presented as mean±SEM, representative images for Oil red O- FIG. 4B, Mac-3- FIG. 4C, α-actin- FIG. 4E and picro-sirius-red FIG. 4F—specific staining, as well as representative en face aortas stained for Oil red O, shown on the right. Scale bar 1000 μm (FIG. 4A, FIG. 4B), 200 μm (FIG. 4C, FIG. 4E, FIG. 4F).

FIG. 5A to FIG. 5C: Bacterial expression of recombinant variants of the Mac-1 !-domain and CD40L. FIG. 5A The human Mac-1 amino residues $R^{115}$ to $S^{340}$, coding for the am I-domain, were produced as soluble His-tag fusion protein (~28 kDa) in a bacterial expression system and purified by immobilized metal affinity chromatography (IMAC). FIG. 5B Contaminating bacterial proteins were further removed by anion-exchange chromatography and increasing concentrations of sodium chloride. Elution fractions containing the isolated I-domain as assessed by Coomassie stains were pooled and dialyzed against PBS. FIG. 5C The TNF homologous region of human CD40L ($E^{108}$ to $L^{261}$)) was produced as c-myc- and His-tag-fusion protein. The protein (~19 kDa) was extracted from insoluble inclusion bodies, purified by IMAC and refolded by subsequent dialysis against PBS. The purity of both protein preparation was >95% as assessed by SDS-polyacrylamide gel. (W) washing fractions, (FT) column flow through, (E) elution fractions, (M) protein size marker.

FIG. 6A to FIG. 6D: Peptide treatment with cM7 did not cause cellular apoptosis and cytotoxicity in vitro and in vivo. (FIG. 6A, FIG. 6B) Macrophages recruited to the peritoneal cavity by thioglycollate where challenged by intraperitoneal injections of either cM7, scM7 or the blocking anti-Mac-1 antibody M1/70. After 4 hours, peritoneal exudates cells were harvested and quantified for annexin V binding and propidium iodide loading. cM7 did not cause an increase of apoptotic or necrotic cells in vivo compared with scM7, whereas the antibody treatment resulted in a significant higher percentage of cellular apoptosis and necrosis in peritoneal macrophages. (FIG. 4C, FIG. 4D) In vitro cultivated human umbilical vein endothelial cells (HUVECs) were incubated with cM7, scM7 or a combination of CD40L or a blocking anti-CD40 antibody. As assessed by caspase 3/7-activity, peptide treatment for 24 hours did not induce cellular cytotoxicity. Apoptosis of endothelial cells, as determined by LDH-release, as slightly increased in CD40L primed HUVECs when incubated with cM7. Data are presented as mean±SEM of at least 3 independent experiments.

FIG. 7A to FIG. 7C: A monoclonal antibody specifically recognizing the CD40L binding site on the Mac-1 I-domain modulates leukocyte recruitment in vitro. Mice were immunized with the linear peptide $V^{160}$-$S^{172}$. FIG. 7A Clone RC3 specifically bound to the immobilized peptide M7, but not to the scrambled version sM7 or the Mac-1 I-domain fragment M8. FIG. 7B Anti-M7 blocked adhesion of Mac-1 expressing CHO cells to immobilized CD40L comparable to the pan I-domain blocking antibody clone 2LPM19c. CHO cells failed to adhere on fibrinogen after pan I-domain blockade, but not after blockade of the linear stretch $V^{160}$-$S^{172}$. FIG. 7C In a dynamic flow chamber assay anti-M7 treatment blocked adhesion of murine RAW246.7 cells to a confluent monolayer of activated endothelial cells compared with the respective IgG-control. Data are presented as mean±SEM of at least 3 independent experiments.

FIG. 8A to FIG. 8I show the effects of cM7-treatment on basic inflammatory properties in vivo. C57/B6-mice were treated with the specific inhibitor of CD40L/Mac-1 interaction, cM7, or with the unspecific peptide control scM7 by intraperitoneal injections. An inflammatory state was induced by injection of TNF-α. (FIG. 8A, FIG. 8B, FIG. 8C).

In an acute model of inflammation (cytokine challenge by TNFα) the compound of the present invention reduced levels of the chemokines CXCL-1 (=MCP-1) and RANTES, both implicated with inflammatory cells resulting in inflammatory diseases including atherosclerosis. On the other hand the more anti-inflammatory TH2 cytokine IL-10 tended to be elevated. An acute model was chosen since cytokine levels in atherosclerotic mice are hardly systemically regulated. Plasma levels of chemokines CXCL-1 and RANTES shifted towards a less inflammatory state, whereas protective IL-10 plasma levels tended to increase in cM7-treated mice. (FIG. 8D, FIG. 8E, FIG. 8F) Activation of leukocyte subsets was evaluated by quantifying the surface expression of the adhesion molecules ICAM-1, -2, and (CD26L) L-Selectin in flow cytometry. TNF-α induced recruitment of monocytes FIG. 8G, neutrophils FIG. 8H and Gr-1-positive inflammatory monocytes FIG. 8I was determined in both groups. Data are presented as mean±SEM of 8 animals per group.

FIG. 9A to FIG. 9J: Effects of long-term peptide treatment on immunological properties in vivo. $LDLR^{-/-}$ mice consumed a high cholesterol diet and were injected with the peptide inhibitor cM7, the control peptide scM7, or saline three times a week for a total period of 20 weeks. (FIG. 9A, FIG. 9B, FIG. 9C, FIG. 9D, FIG. 9E, FIG. 9F) Levels of plasma cytokines IL-6, IL-1, IL-12, TNF-α and IFN-γ were quantified by a cytometric bead assay. T-cell subpopulations (FIG. 9G, FIG. 9H), B-cells FIG. 9I, and Gr-1-positive inflammatory monocytes FIG. 9J were quantified by flow cytometry.

FIG. 10A shows that treatment with an anti-CD40L blocking antibody significantly prolonged tail vein bleeding time by 74±12% $p=0.04$). Interestingly, selective blockade with cM7 did not affect bleeding time, suggesting that CD40L-Mac-1 interaction is specific for CD40L's inflammatory pathways. FIG. 10B shows that cM7 did not prolong vessel occlusion time in a model of arterial thrombosis, whereas anti-CD40L and anti-CD40 treatment impaired thrombus formation in mesenterial arterioles resulting in a prolongation of the occlusion time by 113±22% ($n=5$, $p=0.005$) and 116±22% ($n=4$, $p=0.05$), respectively. FIG. 10C and FIG. 10D show that disruption of the CD40L-Mac-1 interaction by cM7 only caused a slight increase in thromboembolization rate ($n=5$, $p=0.005$). However, this was a negligible effect compared with anti-CD40L and anti-CD40 treatment which increased embolization rate by 339±38% ($n=6$, $p=0.001$), and 173±40% ($n=3$, $p=0.008$), respectively. Interestingly, treatment with neutralizing anti- Mac-1 antibodies also increased the embolization rate—albeit mildly—by 131±41% (n=4, p=0.03.)

EXAMPLE 1

Recombinant Protein Expression.

Mac-1's I-domain was produced as His-tag fusion protein by inserting the DNA-sequence coding for the Mac-1 amino acids $R^{115}$ to $S^{340}$ in pET20b (Novagen), and subsequent purification by Ni-NTA immobilized metal affinity chromatography (Qiagen) and anion-exchange chromatography using Q-Sepharose (GE Healthcare). CD40L was produced as His- and c-myc-tag fusion protein by inserting the coding DNA for amino acids $E^{108}$ to $L^{261}$ in pHOG-21[34]. CD40L was purified by Ni-NTA immobilized metal affinity chromatography.

The Mac-1 I-domain was produced as fusion protein containing an C-terminal His-tag by inserting the DNA-sequence coding for the Mac-1 amino acids $R^{115}$ to $S^{340}$ in the expression vector pET20b (Novagen) by a PCR-based strategy using the following primers: 5'-AGAAGTTCCCAGAGGCCCT-3' (SEQ ID NO:4) and 5'-GAGTGCGGCCGCGGCAGCGCT-GAAGCCTTCCTG-3' (SEQ ID NO:5). A CHO cell line constitutively expressing the entire human Mac-1 α-chain served as template. The resulting PCR-fragment was cloned in pGEMT (Promega), released by NcoI and NotI (New England Biolabs) and inserted into the NcoI-NotI-linearized pET20b. This expression vector was transformed in BL-21 DE Star (Invitrogen) and expressed by addition of 0.5 mM IPTG (Sigma). The protein was extracted by BugBuster lysis (Novagen) and subsequently purified by Ni-NTA immobilized metal affinity chromatography (Qiagen) in a standard FPLC-system (GE Healthcare). After elution of the target protein by 250 nM imidiazol (Sigma) the fraction containing the Mac-1 I-domain (~28 kDa) was dialyzed against 20 mM Tris-Cl, 20 mM NaCl, pH 8.0 and further purified by anion-exchange chromatography on a Q-Sepharose-columns (GE Healthcare). CD40L was produced as fusion protein containing a N-terminal His- and c-myc-tag, as well as a trimerization domain.

The coding DNA sequence for amino acids $E^{108}$ to $L^{26}$ were amplified by PCR using the following primers: 5'-CCTAGGCGGCCGCTATCAGAGTTTGAGTAAGC-CAAAGGAC-3' (SEQ ID NO:6) and 5'-CTTCTAGA AAACAGCTTTGAAATGCAAAAAGA-3' (SEQ ID NO:7). A cDNA clone coding for the human CD40L (Origene) served as template. The His- and c-myc-tag were amplified by the following primers: 5'-CCGGC-CATGGCCGAACAAAAGCTGATCTCAGAAGAAG-3' (SEQ ID NO:8) and 5'-TGAG GTACCTAGGTGATGGT-GATGGTGATGTGAG-3' (SEQ ID NO:9). As template for the trimerization domain served the primer 5' ATGAAACA-GATTGAAGATAAAATTGAAGAAATTCT-GAGCAAAATTTATCATATTGA AAACGAAAT-TGCGCGTATTAAAAAACTGATTGGAGAA-3' (SEQ ID NO:10). All PCR fragments were cloned into pGEMT and released by NcoI, KpnI (His- and c-myc-Tag), KpnI and XbaI (trimerization motif) and XbaI and NotI (CD40L). Fragments were subsequently cloned into the expression vector pHOG-21 (Schwarz et al., Circ. Res., 2006, p. 25-33) and transformed into TG-1 bacteria (Promega). CD40L was expressed after induction with 1 mM IPTG. Proteins were extracted as insoluble inclusion bodies, solubilized in 7 M Urea, 100 mM NaH2PO4, 100 mM Tris-Cl, pH 8.0 and purified under denaturing conditions by Ni-NTA immobilized metal affinity chromatography. CD40L was refolded by dialysis against decreasing Urea-concentrations. Both proteins were finally dialyzed against PBS and stored at −80° C. until further use. The purity of both recombinant proteins was >90% as assessed by SDS gel electrophoresis.

Because most of Mac-1's ligands—such as fibrinogen, ICAM-1, GPIbα, RAGE, C3bi, or heparin—bind to the Mac-1 I-domain, a stretch of ~200 amino acids within the am subunit of the integrin (FIG. 1*a*), it was hypothesized that the I-domain also serves as binding partner for CD40L. To test this hypothesis, recombinant variants of the I-domain and CD40L were produced as shown in FIG. 5.

In a solid phase binding assay, CD40L, either soluble or immobilized, specifically bound to the isolated I-domain (FIG. 1*b,c*). A $K_d$ of ~66 nM revealed a high-affinity interaction comparable to the affinity of CD40L to $\alpha_{IIB}\beta_3$ (~30 nM). To identify the binding site used by CD40L, a peptide mapping strategy using linear peptides M1-M8 was employed, originating from the hydrated surface of the Mac-1 I-domain as shown in Table 1.

TABLE 1

Peptides used

| Peptide | Sequence | I-domain* | Structure | MW (kDa) |
|---|---|---|---|---|
| M1 | PHDFRRMKEFVST (SEQ ID NO: 11) | $P^{147}$-$T^{159}$ | linear | 1.649 |
| M2 | PITQLLGRTHTATGIRK (SEQ ID NO: 12) | $P^{201}$-$K^{217}$ | linear | 1.863 |
| M3 | KFGDPLGYEDVIPEADR (SEQ ID NO: 13) | $K^{245}$-$R^{261}$ | linear | 1.921 |
| M4 | DAFRSEKSRQELNTI (SEQ ID NO: 14) | $D^{273}$-$I^{287}$ | linear | 1.793 |
| M5 | FQVNNFEALKT (SEQ ID NO: 15) | $F^{297}$-$T^{307}$ | linear | 1.310 |
| M6 | QNNPNPRS (SEQ ID NO: 16) | $Q^{190}$-$S^{197}$ | linear | 0.925 |
| M7 | EQLKKSKTL (SEQ ID NO: 1) | $E^{162}$-$L^{170}$ | linear | 1.074 |

TABLE 1-continued

| Peptides used | | | | |
|---|---|---|---|---|
| Peptide | Sequence | I-domain* | Structure | MW (kDa) |
| M8 | EEFRIHFT (SEQ ID NO: 17) | $E^{178}$-$T^{185}$ | linear | 1.078 |
| sM7 | KLSLEKQTK (SEQ ID NO: 18) | n/a | linear | 1.074 |
| cM7 | C-EQLKKSKTL-C (SEQ ID NO: 1) | $E^{162}$-$L^{170}$ | cyclic | 1.280 |
| scM7 | C-KLSLEKQTK-C (SEQ ID NO: 18) | n/a | cyclic | 1.280 |
| FITC-cM7 | C-EQLKKSKTL-C (SEQ ID NO: 1) | $E^{162}$-$L^{170}$ | cyclic, FITC | 1.638 |

*indicates the stretch of the Mac-1 I-domain the peptide corresponds to.

In an initial solid phase binding assay evaluating the binding of the isolated Mac-1 I-domain to immobilized CD40L, the Mac-1 fragments M3, M4, M5, and M7 emerged as potential candidate inhibitors (FIG. 1*f*). In the more physiological setting with the entire Mac-1 protein in a cell membrane environment, M7 most efficiently blocked adhesion of THP-1 cells to CD40L. The extent of inhibition resembled that of a pan I-domain blocking antibody (FIG. 1*g*). Moreover, M7 was the only peptide blocking binding of CD40L to human granulocytes and monocytes in flow cytometry (FIG. 1*h*). Finally, M7 mediated direct binding to CD40L in a solid phase binding assay (FIG. 1*i*), and neutralized binding of CD40L to chinese hamster ovarian cells expressing constitutively activated Mac-1 (Mac-1-CHO) (FIG. 1*j*). M7 concentration dependently blocked the binding of CD40L to the I-domain with an IC50 of ~4 μM (FIG. 2*a*).

Interestingly, the stretch of amino residues within the Mac-1 I-domain corresponding to the peptide M7, $E^{162}$-$L^{170}$, resides on an exposed loop between the α1 helix and β-sheet B in the tertiary structure, and has not been implicated in binding of the alternative Mac-1 ligands GPIbα, NIF, C3bi, ICAM-1, or fibrinogen. This suggests a distinct binding site for CD40L, and thus the potential to block this interaction selectively. We modified peptide M7 by adding two flanking cysteine residues and subsequent cyclization (cM7) to augment plasma stability in vivo. A scrambled peptide, scM7, served as control (see Table 1). To assess specificity of this peptide inhibitor, the adhesion of Mac-1-CHO cells to different Mac-1 ligands in the flow chamber was tested. While cM7 potently blocked cellular adhesion to CD40L (FIG. 2*b*), it did not affect adhesion to ICAM-1 and GPIbα (FIG. 2*c,d*). In contrast, M2—but not M7—blocked the interaction between Mac-1 and GPIbα, as previously described, while not affecting CD40L-Mac-1 binding. Moreover, cM7 did not alter binding of CD40 to CD40L (FIG. 2*e*). Also, cM7-treatment did not induce apoptosis or cytotoxicity in vitro and in vivo, suggesting good tolerability of these agents as shown in FIG. 6.

To provide further evidence on the specific importance of the region $E^{162}$-$L^{170}$ for CD40L/Mac-1 binding, a monoclonal antibody against the peptide $V^{160}$-$S^{172}$, termed anti-M7 was raised. An antibody specific to a peptide corresponding to the human Mac-1 I-domain sequence V160-S172 (termed anti-M7) was obtained by immunizing mice with the peptide C-VMEQLKKSKTLFS-NH2 (SEQ ID NO:3) coupled to diphtheria toxoid (Monash Antibody Technologies Facility, Monash University, Melbourne, Australia). Solid phase assays demonstrated high anti-sera binding to immobilized peptide M7. This antibody specifically bound to M7, but not to the scrambled version sM7 or M8, another Mac-1 fragment of similar length. Anti-M7 blocked the adhesion of Mac-1-CHO cells to immobilized CD40L, but not to fibrinogen (FIG. 7).

Furthermore, FITC-labeled cM7 concentration-dependently bound to murine fibroblasts over-expressing CD40L, but not to respective mock-transfected control cells (FIG. 2*f*).

EXAMPLE 2

Solid phase binding assay. Recombinant CD40L was incubated with immobilized Mac-1 I-domain in the presence or absence of blocking peptides. Binding of sCD40L was detected by addition of anti-cmyc-HRP (Invitrogen), TMB-substrate (Pierce), and colorimetric reaction. Alternatively, CD40L (Provitro) was immobilized, and binding of the recombinant Mac-1 I-domain was quantified by addition of anti-His-Biotin (Qiagen), and HRP-coupled streptavidin (Pierce). For the binding to immobilized peptides, CD40L was biotinylated with the Micro Biotinylation Kit (Sigma). A mixture of equal molarities of all peptides served as the positive control in this assay.

The recombinant Mac-1 I-domain was immobilized in 96-well plates (Nunc) in PBS at 4° C. overnight. After blocking in 2% BSA/PBS and subsequent washing with PBS, recombinant CD40L was added to the wells in the indicated concentrations and incubated for 2 hours at 37° C. Effect of the peptides M1-M8 was assessed by incubating CD40L (10 μg/ml) in the presence of peptides (50 μM). After removing of unbound CD40L by washing with 0.1% Tween-20/PBS, anti-c-myc-HRP (Invitrogen) was added and incubated for 2 hours at room temperature. Binding was quantified by addition of TMB-substrate (Pierce), colorimetric reaction at 450 nm. Alternatively, CD40L without a His-tag (Provitro) was immobilized and blocked as described above. Binding of the recombinant Mac-1 I-domain was quantified by addition of anti-His-Biotin monoclonal antibody (Qiagen), HRP-coupled streptavidin (Pierce) and colorimetric reaction at 450 nm. For the specific binding of the Mac-1 I-domain BSA-coated wells were subtracted from the CD40L-coated. $K_d$ was estimated using a one-site binding hyperbola nonlinear regression model with the Software Prism (Graphpad). For quantification of the binding of CD40L to peptides, peptides were immobilized in 96-well plates overnight at 4° C. in 50 mM sodium carbonate, pH 10.6. CD40L was biotinylated using the Micro-Biotinylation-Kit (Sigma) following the manufacturer's instructions and detected by HRP-coupled streptavidin (Pierce) and colorimetric reaction. A mixture of equal molarities of all peptides served as positive control. Absorbance on BSA-coated wells served as negative control and was subtracted.

EXAMPLE 3

3.1 Dynamic and Static Adhesion Assays.

96-well plates (Nunc) were coated with sCD40L and incubated with CHO cells expressing constitutively activated Mac-1, as described previously, or THP-1 cells. Cells were allowed to adhere for 20 to 50 minutes. Blocking antibodies (10 μg/ml) were pre-incubating with the cells. As indicated, assays were carried out in the presence of peptides (50 μM). Permeabilization buffer (6 mg/ml phosphatase substrate (Sigma), 1% Triton X-100, 50 mM sodium acetate, pH 5.5) was added to quantify adhering cells by colorimetric reaction. Alternatively, adhering cells were counted. Murine EC were isolated as previously described. Mac-1 expressing CHO were loaded with CFDA-SE (Invitrogen), allowed to adhere for 45 minutes, and quantified under the fluorescence microscope. For dynamic adhesion assays, 35-mm dishes were coated with 1% BSA, or CD40L, GPIbα (Abnova), fibrinogen (Sigma), or ICAM-1 (R&D systems). Adhering and rolling cells were quantified in a parallel flow chamber system (Glycotech) at the indicated shear rates and in the presence of the indicated peptides (1 μM) or antibodies (10 μg/ml). Alternatively, adhesion and rolling of peritoneal exudate cells on isolated murine endothelial cells were observed.

3.2 Static Adhesion Assays.

96-well plates (Nunc) were coated with sCD40L (10 μg/ml) in PBS overnight at 4° C. After removal of unbound CD40L by washing with PBS, plates were blocked with 0.1% agarose for 1 hour at room temperature and washed with PBS. Blocking antibodies against CD40L (10 μg/ml) were given to the wells as indicated and incubated for 15 min at room temperature, followed by subsequent washing with PBS. CHO cells expressing constitutively activated Mac-1[4] or THP-1 cells were pre-incubated with function blocking antibodies against CD11b or CD11a (10 μg/ml) for 15 min at room temperature. $5\times10^4$ cells/well were allowed to adhere for 20 to 50 min at 37° C. As indicated, static adhesion assays were carried out in the presence of peptides at a concentration of 50 μM. After removal of unbound cells by washing with PBS, permeabilization buffer (6 mg/ml phosphatase substrate (Sigma), 1% Triton X-100, 50 mM sodium acetate, pH 5.5) was added for 1 hour at 37° C. and adhering cells were quantified by colorimetric reaction at 405 nm. Alternatively, adhering cells were counted under the microscope (Zeiss). Alternatively, human umbilical vein endothelial cells (HUVECs) were stimulated with 50 ng/ml TNF-α prior to the experiment. Mac-1 expressing CHO were loaded with carboxyfluorescein diacetate succinimidyl ester (CFDA, Invitrogen) according to the manufacturer's protocol. HUVECs or CHO-cells were selectively incubated with blocking antibodies (10 μg/ml) as indicated, washed and cells were allowed to adhere on HUVECs for 35 min at 37° C. After removal of unbound cells by washing with PBS adhering cells were counted under the fluorescence microscope.

EXAMPLE 4

4.1 Flow Cytometry.

Flow cytometric analysis, platelet activation assays, and quantification of leukocyte-platelet aggregates, were performed as previously described (Zirlik et al., 2007). Binding of cM7 to CD40L-expressing murine fibroblasts was determined by quantification of FITC-coupled cM7. Binding of CD40L to Mac-1 expressing CHO-cells or human leukocytes was performed by incubation with CD40L (10 μg/ml) and subsequent detection with anti-PentaHis antibody (Qiagen).

4.2 Laminar Flow Chamber Assay.

For dynamic adhesion assays, 35 mm dishes were coated overnight at 4° C. with 1% BSA, CD40L, GPIbα (Abnova), ICAM-1 (R&D systems) or fibrinogen (Sigma), at a concentration of 10 μg/ml, and 30 μg/ml, respectively. Adhesion and rolling of Mac-1 expressing CHO-cells was tested in a parallel flow chamber system (Glycotech) using increasing flow rates from 0.5 dyne/cm$^2$ (venous flow) up to 15 dyne/cm$^2$ (arterial flow). Cells were quantified under the microscope (Olympus). As indicated, effects of inhibitors were tested at the indicated shear rates and in the presence of the indicated peptides (1 μM) or antibodies (10 μg/ml). Alternatively, murine endothelial cells were isolated and TNF-α stimulated as described above. Adhesion and rolling of peritoneal exudate cells on isolated murine endothelial cells was quantified as described above. Rolling velocity was computed employing Image Pro cell tracking tool (Media Cybernetics)

4.3 Flow Cytometry.

Flow cytometric analyses, as well as platelet activation assays and quantification of leukocyte-platelet aggregates were performed as previously described (Quezada et al., Ann. Rev. Immunol. (2004), pp 307-328). Briefly, murine blood samples were taken by intracardiac puncture. Red cells were lyzed in 155 mM NH4Cl, 5.7 mM $K_2HPO_4$, 0.1 mM EDTA, pH 7.3. Leukocytes were resuspendet in 0.1% BSA/PBS and Fc-Receptors were blocked by anti-CD16/CD32 antibodies (Ebioscience). Antibodies for epitope specific fluorescence-activated cell sorting (FACS Calibur, BD) included anti-CD11b, anti-CD115, anti-Gr-1, anti-CD4, anti-CD8, anti-CD20, anti-CD41, anti-CD62P, anti-CD54, anti-CD102, and anti-CD106 (all from Ebioscience). Binding of cM7 to CD40L- or mock-transfected murine fibroblasts was determined by incubation of FITC-cM7 at the indicated concentrations with cells for 30 min at 37° C. and subsequent quantification of the fluorescence in the FL-1 channel. Binding of CD40L to Mac-1 expressing CHO-cells or human leukocytes was performed by incubation of the with the His-tag-CD40L fusion protein (10 μg/ml) for 30 min at 37° C. in PBS+$Ca^{2+}$/$Mg^{2+}$ and subsequent detection with Alexa488-labeled anti-PentaHis (Qiagen). Human monocytes and granulocytes were gated based on their properties in the forward- and sideward scatter. For the analysis of the endothelial expression of adhesion molecules, cells were TNF-α stimulated for 24 hours, detached using accutase (Sigma) and incubated with fluorochrome-coupled antibodies.

EXAMPLE 5

Cytokine Challenge.

8 weeks old C57BL/6J mice received an intraperitoneal injection of 200 ng of murine TNF-α (R&D systems) and 100 μg either of the peptides cM7, scM7 or an equal volume of sterile saline. After 5 hours mice were euthanized with $CO_2$. The peritoneal cavity was flushed with 2 ml PBS and supernatant was screened for cytokines. Blood was collected by an intracardial puncture. Plasma concentrations of IL-6, IL-10, IL-12p70, TNF-α, IFN-γ, MCP-1, KC, and RANTES were determined by the Cytometric Bead Array (CBA, BD Biosciences) according to the manufacturer's instructions. Activation of peripheral leukocytes and platelets was assessed by flow cytometry as described above.

EXAMPLE 6

Oxidative Stress Assay.

Murine leukocytes were pre-incubated with Dihydrorhodamine (Invitrogen) according to the manufacturer's instructions and formation of reactive oxidative stress was monitored by flow cytometry.

EXAMPLE 8

Murine Peritonis Model.

WT or CD40L$^{-/-}$ mice (Jackson Laboratories) received an injection of 2 ml of 4% thioglycollate broth (Sigma). A peritoneal lavage was performed after 15 hours by flushing the peritoneal cavity with PBS. Peritoneal exudate cells (PECs) were quantified after red cell lysis.

EXAMPLE 9

Intravital Microscopy.

Mice received an intraperitoneal injection 5 hours before surgery of 200 ng of murine TNFα (R&D systems) and 100 μg of peptides dissolved in sterile saline 5 hours before surgery. Mice were anesthetized with an intraperitoneal injection of ketamine hydrochloride (Essex) and xylazin (Bayer) at a dose at 187.5 mg/kg of body weight and 62.5 mg/kg of body weight, respectively. The cremaster muscle was exteriorized as described previously (Iezzi et al., PNAS (2009), pp 876-881). For some experiments a catheter was placed in the jugular vein and peptides were administered during microscopy. The cremaster was superfused with thermo-controlled (36° C.) saline. Mice were placed on a heating pad to maintain body temperature. Videos were taken with an intravital microscope (AxioScope Vario, Carl Zeiss) fitted with a saline immersion objective (WPlan-APOCHROMAT 20x/1,0DIC IR, Carl Zeiss) a high sensitivity camera system (AxioCam MRm, Carl Zeiss) for 30 seconds each. Rolling leukocyte flux was defined as the number of leukocytes moving at a velocity less than erythrocytes. Leukocyte rolling velocity was measured by the average time required for leukocytes to roll over a defined length of the venule at each time point. Adherent leukocytes were defined as cells that remained stationary for at least 30 s. Rolling leukocyte flux, adhering flux were quantified by a blinded investigator.

EXAMPLE 10

Atherogenesis study. Eight-week-old male LDL-receptor-deficient (LDLr$^{-/-}$) mice (Jackson Laboratories) consuming a high-cholesterol diet (HCD) were treated with intraperitoneal injections of the peptides cM7, scM7 (Peptide Specialty Laboratory) in a dose of 100 μg, or sterile saline three times a week. After 20 weeks blood samples were taken for flow cytometric analysis of leukocyte subpopulations, cholesterol and triglyceride plasma levels, as well as for the determination of plasma cytokines and chemokines. Blood pressure was determined by a non-invasive blood pressure measurement (NIBP, Harvard Apparatus). Mice were euthanized, and aortic roots and arches were frozen in OCT (OCT compound; Tissue-Tek). Thoracic and abdominal aortas were fixed in 10% buffered formalin. Serial cryostat sections (6 μm) of mouse aortic tissues were fixed in acetone, and air-dried. Nonspecific binding was blocked with 5% species-appropriate normal serum (Vector Laboratories). Sections were then incubated with primary antibodies diluted in phosphate-buffered saline, supplemented with 5% species-appropriate normal serum. Incubation with secondary antibodies was followed by avidin-biotin complex (ABC, Vector Laboratories). Antibody binding was visualized with 3-amino-9-ethylcarbazole (AEC; Dako), followed by counterstaining with Gill's hematoxylin solution (Sigma-Aldrich). Control stainings included staining with the respective IgG isotypes (Pharmingen, Dako). Antibodies used were rat anti-mouse Mac-3 for macrophage specific staining, anti α-actin for smooth muscle cell specific staining (Dako). For the visualization of Type I Collagen, Formalin-fixed frozen sections were incubated for 4 hours in a freshly prepared 0.1% solution of picrosirius red (Polysciences) in saturated aqueous picric acid. After rinsing in 0.01 N HCl and distilled water, sections were dehydrated in 70% ethanol and mounted in Permount (Vector Laboratories). Picrosirius red staining was analyzed by polarization microscopy. As the color of collagen fibers assessed in the picrosirius red staining depends on the thickness of collagen fibers and changes from green (thin fibers) to yellow, orange, and red (thick fibers), color distribution in stained collagen sections was quantified. Deposition of lipids was determined by oil red O staining after formalin fixation in aortic sections or in en face preparations of the abdominal aorta. To quantify the composition of the aortic lesions, sections of the aortic tissue were analyzed microscopically in all mice. Within the aortic root, lesion areas were analyzed in cross-sections obtained at the level of all 3 leaflets of the aortic valve, immediately proximal to the right coronary artery ostium. The total aortic wall area, lesion area in the aortic root, and the percentage of area stained for macrophages, lipids, SMCs, or collagen were determined via computer-assisted image quantification (ImagePro, Media Cybernetics).

EXAMPLE 11

11.1 Pharmakokinetics of the Peptide Inhibitor.

C57BL/6J mice were injected intraperitoneal with FITC-labeled cM7. Fluorescence in Plasma samples was measured at the indicated time points in Fluorescence Plate Reader (Spectramax). CM7-FITC diluted in plasma samples served as standard.

11.2 Structural Modeling.

Mac-1 I-domain structure was visualized using Sirius visualization system 1.2 (San Diego Supercomputer Center) and a crystallographic dataset for the Mac-1 I-domain (PDB ID: 1NA5).

11.3 Antibodies and Peptides.

Epitope-specific antibodies were purchased as follows: anti-human CD11b, clone 2LPM19c (Santa Cruz Biotechnology); anti-human CD11b, clone ICRF44 (Biolegend); anti-human CD11a, clone HI111 (Biolegend); anti-human CD40L, clone 24-31 (Calbiochem); anti-human CD40L, clone 40804 (R&D systems); anti-human ICAM-1, clone BBIG-11 (R&D systems). Peptides were synthesized from Peptide Specialty Laboratories (Heidelberg), purified by HPLC, and cyclisized, if applicable. Molecular mass was determined by mass spectrometry. Peptides had a purity >95%.

11.4 Cell Culture.

Human umbilical vein endothelial cells (HUVECs) were purchased from Lonza and grown in M199, 20% fetal calf serum (FCS), 1% Penicillin/Streptomycin, 0.1% Fungizone, 1% non-essential amino acids (NEAA), 1% Na-Pyruvat, 1% Heparin, 1% ECGS. Monocytic THP-1 were cultured in RPMI 1640, 1% Penicillin/Streptomycin, 10% FCS, 0.05 mM 2-Mercaptoethanol. CHO cells expressing constitutively activated Mac-1 have been described previously[1] and were cultured in DMEM, 1% Penicillin/Streptomycin, 10% FCS, 1% NEAA, 1% L-Glutamin, 125 μg/ml Zeocin, 70 μg/ml Geniticin. CD40L- and mock-transfected murine fibroblasts were a gift from Dr. K. Zirlik (University of Freiburg, Department for Hematology, Freiburg, Germany) and were cultured in DMEM, 1% Penicillin/Streptomycin, 10% FCS, 1% NEAA, 1% L-glutamin, 125 μg/ml.

11.5 Isolation of Murine Endothelial Cells.

For isolation of murine endothelial cells corresponding wildtype or $CD40L^{-/-}$ mice (all C57BL/6J) were euthanized with $CO_2$, and lungs, heart, brain, and liver were harvested employing sterile techniques, minced with a razor blade, and digested in 0.2% collagenase type-1/1% BSA (Worthington, Lakewood, N.J. and Sigma, St. Louis, Mo.) for 90 min at 37° C. After washing with 0.1% BSA and filtering through a 70 μm nylon mesh, cells were resuspended in 0.1% BSA and incubated with an anti-mouse CD31 antibody conjugated to sheep anti-rat Dynabeads (Dynal Biotech, Oslo, Norway) for 10 min at room temperature. Cells were then separated and washed three times using a magnetic particle concentrator (Dynal Biotech) and seeded into gelatin-coated plates. After they reached confluence, a second magnetic sorting was performed with a rat anti-mouse ICAM-2 antibody (BD Pharmingen). Cells were grown in DMEM high glucose supplemented with 20% fetal bovine serum (FBS), 1% sodium pyruvate, 1% heparin, 1% bovine endothelial growth factor, 0.6% NEAA, and 1% penicillin/streptomycin. Cells were maintained in M-199 supplemented with 0.1% FBS 24 h prior to experiments.

12. RESULTS OF THE EXAMPLES

The results of the above-described experiments are summarized and shown in the figures and explained in the legend to the figures and furthermore below:

Therapeutic application of peptides in vivo requires adequate plasma availability. Following intraperitoneal injection, cM7 persisted in plasma between 30 minutes and 4 hours (FIG. 2*g*). It was tested whether the peptide inhibitor effectively modulated inflammatory functions in vivo. Upon treatment with cM7, mice challenged with TNFα intraperitoneally expressed lower plasma levels of MCP-1, and by tendency also of CXCL-1 and RANTES, while IL-10 levels increased both in plasma and in peritoneal fluid (FIG. 2*h,i*; FIG. 8 *a-c*). Treatment with cM7 also attenuated TNFα-induced granulocytic oxidative burst (FIG. 2*j*) and reduced platelet L-selectin expression, as well as aggregates of granulocytes/monocytes and platelets (FIG. 2*k,l*), demonstrating various anti-inflammatory properties of the agent of the present invention.

Because Mac-1 classically functions as an adhesion factor in inflammatory diseases, it was hypothesized that cM7 may limit inflammatory cell recruitment. Indeed, cM7 potently decreased thioglycollate-elicited peritoneal cell accumulation in wild-type mice, but not in $CD40L^{-/-}$ mice (FIG. 3*a*). Mechanistically, adhesion of Mac-1-CHO and human endothelial cells could be abrogated by selective blockade of CD40L on EC or Mac-1 on CHO cells, but not vice versa, rendering the interaction between endothelial CD40L and leukocyte Mac-1 the most likely target for our peptide.

Anti-CD40L treatment blocked adhesion to the same extent as did treatment with anti-ICAM-1 or anti-Mac-1 (FIG. 3*c*). CD40L, unlike fibrinogen, preferably bound cells under physiological flow (FIG. 3*d*). Accordingly, CD40L-deficient EC were highly impaired in recruiting murine leukocytes in the flow chamber (FIG. 3*e-g*), an effect not caused by an altered expression of adhesion molecules (FIG. 3*h*). Similarly, anti-M7 prevented leukocyte adhesion to activated EC (FIG. 7).

Finally, intraperitoneal injection of cM7 potently reduced rolling and firm adhesion in cremaster vessels of mice challenged with TNFα (FIG. 3*i-k*), while blood pressure, leukocyte, or platelet counts did not change (see Table 2).

TABLE 2

Intravital Microscopy Study Characteristics

| | saline | $p^1$ | cM7 | $p^2$ | scM7 | $p^3$ |
|---|---|---|---|---|---|---|
| Mice (n) | 12 | n/a | 10 | n/a | 9 | n/a |
| Venules (n) | 93 | n/a | 87 | n/a | 66 | n/a |
| Diameter of venules (μm) | 41.3 ± 16.7 | 0.08 | 37.0 ± 15.8 | 0.74 | 37.4 ± 15.3 | 0.21 |
| Systolic blood pressure (mmHg) | 104.0 ± 12.7 | 0.17 | 97.6 ± 6.5 | 0.71 | 99.5 ± 14.3 | 0.46 |
| Heart rate (bpm) | 653 ± 58 | 0.34 | 628 ± 63 | 0.24 | 659 ± 47 | 0.80 |
| Leukocytes (×1000/μl) | 11.9 ± 2.5 | 1.0 | 11.9 ± 2.3 | 0.44 | 13.0 ± 3.3 | 0.42 |
| Platelets (×1000/μl) | 666 ± 150 | 0.12 | 552 ± 174 | 0.5 | 600 ± 98 | 0.28 |

Data are expressed as mean ± SD.
[1]p-value saline vs. sM7,
[2]p-value cM7 vs. scM7,
[3]p-value scM7 vs. saline.

Similar data were obtained when cM7 was injected intravenously (FIG. 3I).

Collectively, these data identify CD40L/Mac-1 interaction as a powerful regulator of leukocyte recruitment in vivo susceptible to effective and specific targeting by cM7.

The recruitment of monocytes contributes critically to the initiation and progression of most chronic inflammatory diseases. It was therefore tested whether the peptide inhibitor could mitigate atherosclerosis in vivo in mice. $LDLr^{-/-}$ mice consuming a high-cholesterol diet for 20 weeks developed significantly smaller lesions both in the aortic sinus and abdominal aorta when treated with cM7 (FIG. 4*a*, 4*b*).

Beyond a mere reduction in size, atherosclerotic plaques from cM7-treated animals contained significantly fewer macrophages and lower lipid accumulation, while smooth-muscle cells increased (FIG. 4*c-e*). Collagen content increased in plaques of both the treatment group and the control group (FIG. 4*f*), but consisted of a higher percentage of stable, large collagen fibers in that of cM7-treated animals (FIG. 4*g*). This result shows that genetic or therapeutic inhibition of CD40L attenuates atherosclerotic lesion formation and remodels the plaque toward a morphology with more characteristics of stability. Any changes in immunologic characteristics were not observed—such as numbers of T cells, B cells, or cytokines—indicating a Th1-/Th-2 phenotype—such as IL-10, IL-12, or INFγ—upon long-term treatment with cM7 (FIG. 9).

Lipid levels, weight, leukocyte subsets, blood pressure, cytokine levels, and chemokine levels remained unchanged (see Table 3).

TABLE 3

Atherosclerosis Study Characteristics

| | | saline | p[1] | cM7 | p[2] | scM7 | p[3] |
|---|---|---|---|---|---|---|---|
| Weight (g) | BF | 23.8 ± 1.7 | 0.57 | 23.4 ± 2.3 | 0.23 | 24.2 ± 1.2 | 0.44 |
| | AF | 36.4 ± 3.8 | 0.65 | 35.7 ± 3.8 | 0.74 | 35.3 ± 2.2 | 0.37 |
| Cholesterol (mg/dl) | AF | 96.6 ± 29.7 | 0.63 | 91.5 ± 30.5 | 0.97 | 91.0 ± 33.6 | 0.65 |
| Triglycerides (mg/dl) | AF | 228 ± 97 | 0.18 | 277 ± 107 | 0.20 | 201 ± 190 | 0.63 |
| Visceral fat pads (g) | BF | 2.3 ± 0.7 | 0.96 | 2.3 ± 0.7 | 0.81 | 2.2 ± 0.5 | 0.77 |
| Systolic blood pressure (mmHg) | AF | 103 ± 12 | 0.23 | 98 ± 7 | 0.79 | 97 ± 13 | 0.25 |
| Heart rate (bpm) | AF | 655 ± 54 | 0.44 | 638 ± 58 | 0.29 | 660 ± 42 | 0.80 |
| Leukocytes | BF | 12.1 ± 2.8 | 0.41 | 11.2 ± 3.1 | 0.13 | 13.3 ± 3.9 | 0.35 |
| (×1000/μl) | AF | 5.23 ± 1.31 | 0.17 | 4.54 ± 1.28 | 0.90 | 4.62 ± 1.68 | 0.29 |
| Platelets (×1000/μl) | BF | 557 ± 153 | 0.51 | 529 ± 53 | 0.25 | 562 ± 91 | 0.93 |
| | AF | 663 ± 138 | 0.01 | 486 ± 198 | 0.30 | 556 ± 135 | 0.05 |
| CD11b+ (% of leukocytes) | AF | 16.8 ± 6.5 | 0.33 | 14.3 ± 4.4 | 0.68 | 13.4 ± 5.6 | 0.19 |
| Granulocytes (% of leukocytes) | AF | 13.9 ± 4.3 | 0.60 | 13.0 ± 3.3 | 0.93 | 13.2 ± 4.8 | 0.70 |
| Monocytes (% of leukocytes) | AF | 9.8 ± 3.6 | 0.06 | 7.2 ± 2.1 | 0.50 | 6.4 ± 3.1 | 0.03 |

Data are expressed as mean ± SD.

[1]p-value saline vs. sM7,

[2]p-value cM7 vs. scM7,

[3]p-value scM7 vs. saline,

AF: after feeding,

BF: before feeding.

EXAMPLE 12

Potential side effects were checked in an in vivo thrombosis model. 3-4 weeks old C57BL/6J mice received an intraperitoneal injection of either sterile saline (100 μl), the peptides cM7, scM7, or the indicated antibodies. A mesenteric arteriole was chosen and injured with ferrichloride. Platelets were stained by retroorbital injection of rhodamine 3G and visualized through an intravital microscope (Axio-Scope Vario, Carl Zeiss). Vessel occlusion time and thrombus embolization rate was analyzed. Tail bleeding time was determined as previously reported (Andre et al., Loc. Cit.).

Haemostatic functioning of CD40L depends on interaction with either CD40 or platelet integrin GPIIb/IIIa ($\alpha_{IIb}\beta_3$) (Andre et al. loc. cit). The inhibition of this interaction by former therapeutic strategies employing antibodies neutralizing total CD40L provoked thromboembolic complications. Thus, confirming previous studies, treatment with an anti-CD40L blocking antibody significantly prolonged tail vein bleeding time by 74±12% p=0.04) in our study. Interestingly, selective blockade with cM7 did not affect bleeding time (FIG. 10A), suggesting that CD40L-Mac-1 interaction is specific for CD40L's inflammatory pathways. Accordingly, cM7 did not prolong vessel occlusion time in a model of arterial thrombosis, whereas anti-CD40L and anti-CD40 treatment impaired thrombus formation in mesenterial arterioles resulting in a prolongation of the occlusion time by 113±22% (n=5, p=0.005) and 116±22% (n=4, p=0.05), respectively (FIG. 10B). Furthermore, disruption of the CD40L-Mac-1 interaction by cM7 only caused a slight increase in thromboembolization rate (n=5, p=0.005). However, this was a negligible effect compared with anti-CD40L and anti-CD40 treatment increasing embolization rate by 339±38% (n=6, p=0.001), and 173±40% (n=3, p=0.008), respectively. Interestingly, treatment with neutralizing anti-Mac-1 antibodies also increased the embolization rate—albeit mildly—by 131±41% (n=4, p=0.03, FIG. 10C, D).

The data show that CD40L specifically binds to a distinct region within Mac-1 I-domain. The peptides disclosed herein blocked binding of CD40L to Mac-1, but did not affect some of the other receptor-ligand interactions. Therefore, the peptides disclosed herein and the antibodies can be used as medicaments which do not have undesired side effects.

The invention claimed is:

1. A method for producing an antibody comprising immunizing a mouse with an epitope consisting of the amino acid sequence SEQ ID NO: 3 under conditions such that the antibody is expressed, and recovering the expressed antibody.

2. The method of claim 1, wherein the antibody specifically recognizes the CD40L binding site on macrophage-1 antigen's (Mac-1) I-domain.

3. The method of claim 2, wherein the antibody specifically inhibits the interaction of CD40L with Mac-1.

4. The method of claim 3, wherein the antibody does not provoke other unspecific and unwanted side effects.

* * * * *